United States Patent [19]
Erion et al.

[11] Patent Number: 5,155,100
[45] Date of Patent: Oct. 13, 1992

[54] PHOSPHONO/BIARYL SUBSTITUTED DIPEPTIDE DERIVATIVES

[75] Inventors: Mark D. Erion, Del-Mar, Calif.; Stéphane De Lombaert, Bernardsville, N.J.

[73] Assignee: Ciba-Geigy Corporation, Ardsley, N.Y.

[21] Appl. No.: 694,533

[22] Filed: May 1, 1991

[51] Int. Cl.$^5$ .................. A61K 37/02; C07F 9/38; C07F 9/40
[52] U.S. Cl. ........................... 514/119; 514/85; 514/89; 514/90; 514/91; 514/95; 514/99; 540/542; 544/157; 544/337; 546/22; 548/413; 549/6; 549/218; 558/170; 558/174; 560/16; 560/41; 562/15
[58] Field of Search .............. 558/170, 174; 562/15; 560/41; 514/119

[56] References Cited

U.S. PATENT DOCUMENTS

| | | | |
|---|---|---|---|
| 4,053,505 | 10/1977 | Dutra | 260/502.5 |
| 4,618,708 | 10/1986 | Roques et al. | 562/448 |
| 4,721,726 | 1/1988 | Berger | 514/464 |
| 4,749,688 | 6/1988 | Haslanger et al. | 514/19 |
| 4,939,261 | 7/1990 | Ksander | 514/357 |
| 4,963,539 | 10/1990 | Delaney | 514/119 |
| 5,021,430 | 6/1991 | Ksander | 514/332 |

FOREIGN PATENT DOCUMENTS

| | | |
|---|---|---|
| 117429 | 9/1984 | European Pat. Off. |
| 54862 | 11/1985 | European Pat. Off. |
| 320118 | 6/1989 | European Pat. Off. |
| 401963 | 12/1990 | European Pat. Off. |
| 419327 | 3/1991 | European Pat. Off. |
| 141930 | 5/1980 | Fed. Rep. of Germany |
| 85196659 | of 1985 | South Africa |
| 85310125 | of 1985 | South Africa |
| 2207351 | 2/1988 | United Kingdom |

OTHER PUBLICATIONS

Res. Comm. in Chem. Pathology and Pharmacology vol. 52, 81 (1986).
Medicinal Research Reviews vol. 5 483-531 (1985).

Primary Examiner—Mary C. Lee
Assistant Examiner—Michael G. Ambrose
Attorney, Agent, or Firm—Norbert Gruenfeld

[57] ABSTRACT

The invention relates to the N-phosphonomethyl-biaryl substituted dipeptide derivatives of formula I

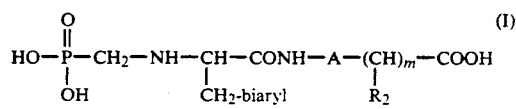

wherein A represents a direct bond, lower alkylene, phenylene or cyclohexylene; m represents 1 or zero, provided that m represents 1 when A is a direct bond; $R_2$ represents hydrogen, hydroxy, lower alkyl, aryl-lower alkyl, $C_5$–$C_7$-cycloalkyl-lower alkyl, amino-lower alkyl, hydroxyl-lower alkyl, lower alkylthio-lower alkyl, lower alkoxy-lower alkyl, aryl-lower alkylthio-lower alkyl or aryl-lower alkoxy-lower alkyl; biaryl represents phenyl substituted by carbocyclic or heterocyclic aryl; and pharmaceutically acceptable mono-, di- or tri-ester derivatives thereof in which one, two or three of the acidic hydroxy groups of the carboxyl and phosphono functional groups are esterified in form of a mono-, di- or tri- pharmaceutically acceptable ester; and pharmaceutically acceptable amide derivatives thereof wherein the carboxyl group is derivatized in form of a pharmaceutically acceptable amide; and pharmaceutically acceptable salts thereof; pharmaceutical compositions comprising said compounds; methods for the preparation of said compounds and for the preparation of intermediates; and methods of treating disorders in mammals which are responsive to the inhibition of neutral endopeptidases by administration of said compounds to mammals in need of such treatment.

21 Claims, No Drawings

PHOSPHONO/BIARYL SUBSTITUTED DIPEPTIDE DERIVATIVES

SUMMARY OF THE INVENTION

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP) EC 3.4. 24.11, also responsible for e.g. the metabolic inactivation of enkephalins.

The aim of the present invention is to provide novel biaryl substituted phosphonic acid derivatives described below which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals, by inhibiting the degradation thereof to less active metabolites. The compounds of the invention are thus particularly useful for the treatment of conditions and disorders responsive to the inhibition of neutral endopeptidase EC 3.4. 24.11, particularly cardiovascular disorders, such as hypertension, renal insufficiency including edema and salt retention, pulmonary edema and congestive heart failure. By virtue of their inhibition of neutral endopeptidase, the compounds of the invention may also be useful for the treatment of pain, depression and certain psychotic conditions. Other potential indications include the treatment of angina, premenstrual syndrome, Meniere's disease, hyperaldosteronism, hypercalciuria, ascites, glaucoma, asthma and gastrointestinal disorders such as diarrhea, irritable bowel syndrome and gastric hyperacidity.

The present invention relates to the N-phosphonomethyl-biaryl substituted dipeptide derivatives of formula I

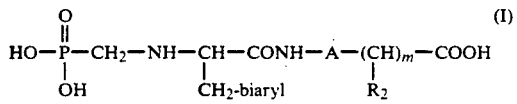

wherein A represents a direct bond, lower alkylene, phenylene or cyclohexylene; m represents 1 or zero, provided that m represents 1 when A is a direct bond; $R_2$ represents hydrogen, hydroxy, lower alkyl, aryl-lower alkyl, $C_5$–$C_7$-cycloalkyl-lower alkyl, amino-lower alkyl, hydroxy-lower alkyl, lower alkylthio-lower alkyl, lower alkoxy-lower alkyl, aryl-lower alkylthio-lower alkyl or aryl-lower alkoxy-lower alkyl; biaryl represents phenyl substituted by carbocyclic or heterocyclic aryl; and pharmaceutically acceptable mono-, di- or tri-ester derivatives thereof in which one, two or three of the acidic hydroxy groups of the carboxyl and phosphono functional groups are esterified in form of a mono-, di- or tri- pharmaceutically acceptable ester; and pharmaceutically acceptable amide derivatives thereof wherein the carboxyl group is derivatized in form of a pharmaceutically acceptable amide; and pharmaceutically acceptable salts thereof; pharmaceutical compositions comprising said compounds; methods for the preparation of said compounds and for the preparation of intermediates; and methods of treating disorders in mammals which are responsive to the inhibition of neutral endopeptidases by administration of said compounds to mammals in need of such treatment.

Pharmaceutically acceptable ester and amide derivatives are preferably prodrug derivatives, such being convertible by solvolysis or under physiological conditions to the free phosphono/carboxylic acids of formula I.

Compounds of formula I and derivatives thereof, depending on the nature of substituents, possess one or more asymmetric carbon atoms. The resulting diastereoisomers and optical antipodes are encompassed by the instant invention.

A specific embodiment of the invention relates to the compounds as defined above wherein biaryl represents phenyl substituted by monocyclic carbocyclic or heterocyclic aryl.

DETAILED DESCRIPTION OF THE INVENTION

More particularly, the present invention is concerned with and has for its object the compounds of formula II

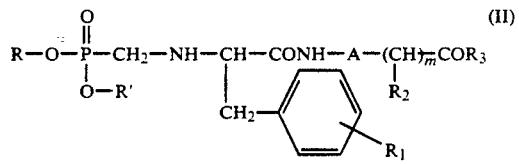

wherein R and R' represent independently hydrogen, carbocyclic aryl, 6-tetrahydronaphthyl, 5-indanyl, acyloxymethyl optionally monosubstituted on methyl carbon by $C_1$–$C_{20}$-alkyl, by $C_5$–$C_7$-cycloalkyl, by aryl or by aryl-lower alkyl; A represents a direct bond, lower alkylene, 1,4-phenylene or 1,4-cyclohexylene; m represents 1 or zero provided that m represents 1 when A is a direct bond; $R_1$ represents phenyl, or phenyl substituted by lower alkyl, lower alkoxy, halogen or trifluoromethyl; or $R_1$ represents thienyl or furanyl optionally substituted by lower alkyl; $R_2$ represents hydrogen, lower alkyl or aryl-lower alkyl; $COR_3$ represents carboxyl or carboxyl derivatized in form of a pharmaceutically acceptable ester or amide; and pharmaceutically acceptable salts thereof.

Preferred are the compounds of formula II wherein R and R' independently represent hydrogen, carbocyclic aryl, (carbocyclic aroyloxy or $C_1$–$C_{20}$-alkanoyloxy)-methyl optionally substituted on the methyl carbon by $C_1$–$C_{20}$-alkyl, by $C_5$, $C_6$ or $C_7$-cycloalkyl or by carbocyclic aryl; $R_1$ represents phenyl or phenyl substituted by lower alkyl, lower alkoxy, halogen or trifluoromethyl; A represents linear lower alkylene or a direct bond; m represents 1; $R_2$ represents hydrogen, lower alkyl or aryl-lower alkyl; $COR_3$ represents carboxyl or carboxyl derivatized in form of a pharmaceutically acceptable ester; and pharmaceutically acceptable salts thereof.

Advantageously $R_1$ is located at the para position.

Particularly preferred embodiments of the invention as described above relate to:

a) compounds wherein A represents a direct bond; m represents 1; and R, R', $R_1$, $R_2$ and $COR_3$ have meaning as defined above.

b) compounds wherein A represents lower alkylene, 1,4-phenylene or 1,4-cyclohexylene; m represents zero; and R, R', $R_1$, $R_2$ and $COR_3$ have meaning as defined above.

Particularly preferred are above said compounds of formula II wherein R and R' independently represent hydrogen, $C_1-C_{20}$-alkanoyloxymethyl or $C_1-C_{20}$-alkanoyloxymethyl substituted on methyl by $C_1-C_{20}$-alkyl, by cyclohexyl, by cyclopentyl or by phenyl.

Also particularly preferred are said compounds of formula II wherein R and R' independently represent hydrogen, 5-indanyl, phenyl, or phenyl substituted by one, two or three substituents selected from lower alkyl, halogen, lower alkoxy, lower alkanoylamino, trifluoromethyl and lower alkoxycarbonyl.

Advantageously, R and R' are either identical, or one of R and R' represents hydrogen while the other of R and R' has any of the other meanings as defined herein.

Also particularly preferred are the said compounds of formula II wherein $COR_3$ represents carboxyl, $C_1-C_{20}$-alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl or 1-(lower alkanoyloxy)-lower alkoxycarbonyl; and pharmaceutically acceptable salts thereof.

Further preferred are any said compounds of formula II having a free carboxyl group, i.e. wherein $COR_3$ represents carboxyl; and pharmaceutically acceptable salts thereof.

A particular embodiment of the invention relates to the compounds of formula IIa

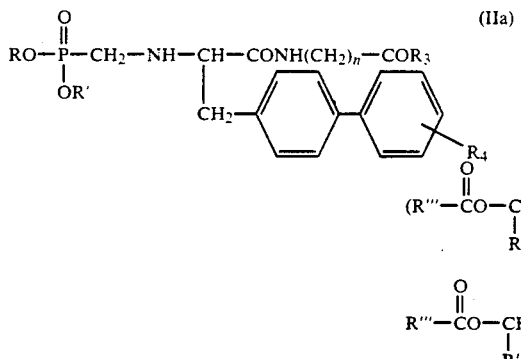

(IIa)

wherein n represents an integer 1 through 6; R and R' independently represent hydrogen, carbocyclic aryl, 5-indanyl or

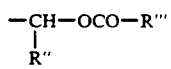

R'' represents hydrogen, $C_1-C_{20}$-alkyl, $C_5$, $C_6$ or $C_7$-cycloalkyl or carbocyclic aryl; R''' represents $C_1-C_{20}$-alkyl, $C_5$, $C_6$ or $C_7$-cycloalkyl, carbocyclic aryl or carbocyclic aryl-lower alkyl; $COR_3$ represents carboxyl, $C_1-C_{20}$-alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl; $R_4$ represents hydrogen, lower alkyl, lower alkoxy, halogen or trifluoromethyl; and pharmaceutically acceptable salts thereof.

Preferred are said compounds of formula IIa wherein n represents the integer 1, 2, 3 or 4, advantageously 1 or 2; and pharmaceutically acceptable salts thereof.

Also preferred are said compounds of formula IIa wherein $COR_3$ represents carboxyl; also preferred are said compounds wherein $R_4$ represents hydrogen; and other symbols have meaning as defined above; and pharmaceutically acceptable salts thereof.

Advantageously, R and R' are either identical, or one of R and R' represents hydrogen while the other of R and R' has any of the other meanings as defined herein.

A preferred embodiment of the invention relates to a compound of formula III

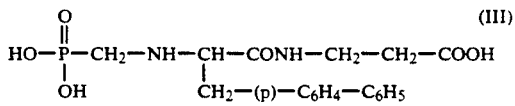

(III)

and pharmaceutically acceptable mono-, di- or tri-ester derivatives thereof in which one, two or three of the acidic hydroxy groups of the carboxyl and phosphono functional groups are esterified in form of a mono-, di- or tri-pharmaceutically acceptable ester; and pharmaceutically acceptable amide derivatives thereof wherein the carboxyl group is derivatized in form of a pharmaceutically acceptable amide; pharmaceutically acceptable salts thereof; and optical or stereoisomers thereof.

The pharmaceutically acceptable ester derivatives are preferably prodrug ester derivatives, such being convertible by solvolysis or under physiological conditions to the free acid of formula III.

Preferred embodiments are compounds of formula IIIa and IIIb

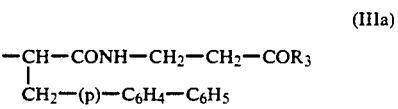

(IIIa)

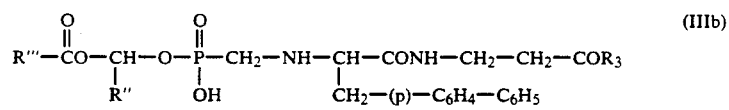

(IIIb)

wherein R'' and R''' independently represent hydrogen, $C_1-C_{20}$-straight chain or branched alkyl, cyclohexyl, cyclopentyl or phenyl; $COR_3$ represents carboxyl; or $COR_3$ represents carboxyl esterified in form of a pharmaceutically acceptable prodrug ester preferably selected from $C_1-C_{20}$-alkoxycarbonyl, (carbocyclic or heterocyclic aryl)-methoxycarbonyl, (di-lower alkylamino)-$C_2$ to $C_4$-alkoxycarbonyl, dihydroxypropyloxycarbonyl protected in form of a ketal, (lower alkoxycarbonyl or di-lower alkylaminocarbonyl)-methoxycarbonyl, 5-indanyloxycarbonyl and 1-(lower alkanoyloxy)-lower alkoxycarbonyl; and pharmaceutically acceptable salts thereof.

Preferred in turn are said compounds of formula IIIa wherein R'' and R''' have meaning as defined above and $COR_3$ represents carboxyl. Also preferred are said compounds of formula IIIb wherein R'' and R''' have meaning as defined above and $COR_3$ represents carboxyl esterified in form of a pharmaceutically acceptable prodrug ester as defined herein.

Other preferred embodiments are the compounds of formula IIIc and IIId

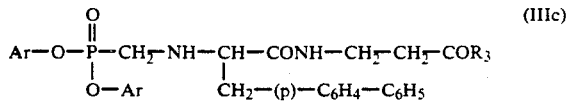

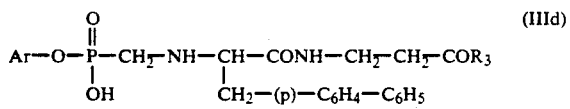

wherein Ar represents phenyl or phenyl substituted by lower alkyl, lower alkoxy, halogen, trifluoromethyl, lower alkanoylamino or lower alkoxycarbonyl; or Ar represents 5-indanyl; $COR_3$ represents carboxyl; or $COR_3$ represents carboxyl esterified in form of a pharmaceutically acceptable prodrug ester preferably selected from $C_1$–$C_{20}$-alkoxycarbonyl, (carbocyclic or heterocyclic aryl)-methoxycarbonyl, (di-lower alkylamino)-$C_2$ to $C_4$-alkoxycarbonyl, dihydroxypropyloxycarbonyl protected in form of a ketal, (lower alkoxycarbonyl or di-lower alkylaminocarbonyl)-methoxycarbonyl, 5-indanyloxycarbonyl, 1-(lower alkanoyloxy)-lower alkoxycarbonyl; and pharmaceutically acceptable salts thereof.

Preferred in turn are said compounds of formula IIIc and IIId wherein $COR_3$ represents carboxyl; and pharmaceutically acceptable salts thereof.

A particular embodiment of the invention relates to compounds having the (S)-configuration at the biarylalanine asymmetric center.

Compounds of the invention can exist in the form of geometric isomers racemates, diastereoisomers, pure enantiomers or mixtures thereof, all of which are within the scope of the invention. In the compounds of the invention, e.g. formulae I, II and III, asymmetric carbon atoms linking the NH and CO groupings of any α-amino acids involved are preferably in the configuration corresponding to that of natural α-amino acids relating thereto, e.g. the biarylalanine moiety has preferably the (S)-configuration as in (L)-phenylalanine. Except for the compounds which are (L)-cysteine derivatives, the asymmetric carbon atom involved is preferably in the (S)-configuration; it is preferably in the (R)-configuration in the case of cysteine derivatives.

The definitions used herein, unless denoted otherwise, have the following meanings within the scope of the present invention.

The term biaryl represents phenyl substituted by carbocyclic aryl or heterocyclic aryl as defined herein, ortho, meta or para to the point of attachment of the phenyl ring, advantageously para; biaryl is also represented at the —$C_6H_4$—$R_1$ substituent in formulae herein.

Carbocyclic aryl preferably represents preferably monocyclic carbocyclic aryl or optionally substituted naphthyl.

Monocyclic carbocyclic aryl represents optionally substituted phenyl, being preferably phenyl or phenyl substituted by one to three substituents, such being advantageously lower alkyl, hydroxy, lower alkoxy, lower alkanoyloxy, halogen, cyano, trifluoromethyl, lower alkanoylamino or lower alkoxycarbonyl.

Optionally substituted naphthyl represents 1- or 2-naphthyl or 1- or 2-naphthyl preferably substituted by lower alkyl, lower alkoxy or halogen.

Heterocyclic aryl represents preferably monocyclic heterocyclic aryl such as optionally substituted thienyl, furanyl, pyridyl, pyrrolyl or N-lower alkylpyrrolyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Aryl as in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy.

Aryl-lower alkyl is advantageously benzyl or phenethyl optionally substituted by one or two of lower alkyl, lower alkoxy, hydroxy, lower alkanoyloxy, halogen or trifluoromethyl.

$C_1$–$C_{20}$-Alkyl represents branched or unbranched alkyl with 1 to 20 carbon atoms.

The term $C_5$–$C_7$-cycloalkyl represents a saturated cyclic hydrocarbon radical which preferably contains 5 to 7 ring carbons and is, preferably cyclopentyl or cyclohexyl.

The term cycloalkyl(lower)alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

Amino-lower alkyl represents preferably amino-(ethyl, propyl or butyl), particularly omega-amino-(ethyl, propyl or butyl).

A di-lower alkylamino group preferably contains 1–4 carbon atoms in each lower alkyl portion and represents, for example, N,N-dimethylamino, N-methyl-N-ethylamino and advantageously N,N-diethylamino.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Lower alkoxycarbonyl-lower alkoxy represents advantageously e.g. 1-(ethoxycarbonyl)ethoxy or ethoxycarbonylmethoxy.

Di(lower)alkylamino-lower alkoxy advantageously represents diethylaminoethoxy.

Hydroxy-lower alkyl is preferably hydroxymethyl.

Lower alkylene represents branched or straight chain alkylene of 1 to 7 carbon atoms, advantageously straight chain (or linear) alkylene, such as methylene, ethylene, propylene, butylene, pentylene or hexylene.

Phenylene represents preferably 1,3 or 1,4-phenylene, advantageously 1,4-phenylene.

Cyclohexylene represents preferably 1,4-cyclohexylene.

Halogen (halo) preferably represents fluoro or chloro, but may also be bromo or iodo.

Lower alkanoyl is preferably acetyl, propionyl, butyryl, or pivaloyl.

Lower alkanoyloxy is preferably acetoxy, pivaloyloxy or propionyloxy.

Acylamino represents preferably lower alkanoylamino, aroylamino, or aryl-lower alkoxycarbonylamino such as benzyloxycarbonylamino.

Lower alkanoylamino is preferably acetamido or propionamido.

Aroyl is preferably benzoyl or benzoyl substituted on the benzene ring by lower alkyl, lower alkoxy, halogen or trifluoromethyl.

Acyl represents preferably lower alkanoyl, carbocyclic aryl-lower alkanoyl, aroyl, lower alkoxycarbonyl or aryl-lower alkoxycarbonyl, advantageously lower alkanoyl. Lower alkoxycarbonyl for acyl is preferably t-butoxycarbonyl (abbreviated t-BOC). Aryl-lower alkoxycarbonyl for acyl is preferably benzyloxycarbonyl (abbreviated CBZ).

Lower alkylidene is preferably isopropylidene.

Cycloalkylidene is preferably cyclohexylidene.

Carboxyl esterified in form of a pharmaceutically acceptable ester, represents advantageously a prodrug ester that may be convertible by solvolysis or under physiological conditions to the free carboxylic acid, such being preferably $C_1$–$C_{20}$-alkoxycarbonyl, advantageously lower alkoxycarbonyl; (amino, acylamino, mono- or di-lower alkylamino)-lower alkoxycarbonyl; carboxy- lower alkoxycarbonyl, e.g. alpha-carboxy-lower alkoxycarbonyl; lower alkoxycarbonyl-lower alkoxycarbonyl, e.g. alpha-lower alkoxycarbonyl-lower alkoxycarbonyl; α-(di-lower alkylamino, amino, mono-lower alkylamino, morpholino, piperidino, pyrrolidino, 1-lower alkylpiperazino)-carbonyl-lower alkoxycarbonyl; aryl-lower alkoxycarbonyl, preferably optionally (halo, lower alkyl or lower alkoxy)-substituted benzyloxycarbonyl, or pyridyl-methoxycarbonyl; 1-(hydroxy, lower alkanoyloxy or lower alkoxy)-lower alkoxycarbonyl, e.g. pivaloyloxymethoxycarbonyl; (hydroxy, lower alkanoyloxy or lower alkoxy)-lower alkoxymethoxycarbonyl; bicycloalkoxycarbonyl-lower alkoxycarbonyl, e.g. bicyclo[2,2,1]-heptyloxycarbonyl-lower alkoxycarbonyl, especially bicyclo-[2,2,1]-heptyloxycarbonylmethoxycarbonyl such as bornyloxycarbonylmethoxycarbonyl; 1-(lower alkoxycarbonyloxy)-lower alkoxycarbonyl; 5-indanyloxycarbonyl; 3-phthalidoxycarbonyl and (lower alkyl, lower alkoxy or halo)-substituted 3-phthalidoxycarbonyl; dihydroxypropyloxycarbonyl wherein hydroxy groups are free or are protected in the form of ketals, e.g. a lower alkylidene, a benzylidene or a 5- or 6-membered cycloalkylidene derivative, advantageously being (2,2-dimethyl-1,3-dioxolan-4-yl)-methoxycarbonyl.

Carboxyl esterified in form of a pharmaceutically acceptable prodrug ester represents most advantageously $C_1$–$C_4$-alkoxycarbonyl, benzyloxycarbonyl optionally substituted on phenyl by lower alkyl, lower alkoxy, halo or trifluoromethyl, 1-($C_2$–$C_4$-alkanoyloxy)-ethoxycarbonyl, (2,2-dimethyl-1,3-dioxolan-4-yl)-methoxycarbonyl, 5-indanyloxycarbonyl, 1-($C_1$–$C_4$-alkoxycarbonyloxy)-ethoxycarbonyl or 3-pyridylmethoxycarbonyl.

Carboxyl derivatized in the form of a pharmaceutically acceptable amide represents preferably carbamoyl or N-substituted carbamoyl, advantageously [lower alkylamino, arylamino, di-lower alkylamino, morpholino, N-lower alkylpiperazino, pyrrolidino, piperidino, perhydroazepino, (amino or acylamino)-lower alkylamino or aryl-lower alkylamino]-carbonyl.

Phosphono derivatized in the form of a pharmaceutically acceptable ester represents mono- or di-esters thereof, preferably phosphono derivatized as mono- or di-prodrug esters such as mono- or di-carbocyclic arylphosphono, e.g. mono- or di-phenylphosphono; mono- or di-5-indanylphosphono; mono- or di-acyloxymethylphosphono optionally substituted on methyl by $C_1$–$C_{20}$-alkyl, by $C_5$–$C_7$-cycloalkyl, by aryl (e.g. phenyl) or by aryl-lower alkyl (e.g. benzyl), and wherein acyloxy represents $C_1$–$C_{20}$-alkanoyloxy, $C_5$–$C_7$-cycloalkanoyloxy, carbocyclic aroyloxy or carbocyclic aryl-lower alkanoyloxy.

Phosphono derivatized as a mono- or di-prodrug esters relates to a mono- or di-pharmaceutically acceptable phosphono ester that may be convertible by solvolysis or under physiological conditions to phosphono (the free phosphonic acid).

Pharmaceutically acceptable salts are either pharmaceutically acceptable acid addition salts for any basic compounds of the invention or salts derived from pharmaceutically acceptable bases for any acidic compounds of the invention.

Pharmaceutically acceptable salts of basic compounds of the invention are acid addition salts, which are preferably such of therapeutically acceptable inorganic or organic acids, such as strong mineral acids, for example hydrohalic, e.g. hydrochloric or hydro-bromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, 1,2-ethanedisulfonic acid, benzenesulfonic, p-toluenesulfonic, naphthalenesulfonic, sulfanilic, cyclohexylsulfamic acid, or ascorbic acid.

Pharmaceutically acceptable salts of the acidic compounds of the invention, e.g. those having a free carboxyl group or a free phosphono hydroxyl group are salts formed with pharmaceutically acceptable bases, e.g. alkali metal salts (e.g. sodium, potassium salts), alkaline earth metal salts (e.g. magnesium, calcium salts), amine salts (e.g. ethanolamine, diethanolamine, triethanolamine, tromethamine salts).

The novel compounds of the invention are pharmacologically potent neutral endopeptidase enzyme inhibitors which inhibit e.g. the degradation of atrial natriuretic factors (ANF) in mammals. They thus potentiate the diuretic and natriuretic effect of exogenous or endogenous ANF in mammals.

The compounds of the invention are thus particularly useful in mammals as diuretic, natriuretic (saluretic) and antihypertensive agents for the treatment of e.g. hypertension, congestive heart failure and edema.

As neutral endopeptidase inhibitors, the compounds are also e.g. enkephalinase inhibitors so as to inhibit the degradation of endogenous enkephalins and may thus also be useful for the treatment of pain in mammals.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-4}$ molar and $10^{-9}$ molar concentrations. The dosage in vivo may range depending on the route of administration, between the 0.01 and 50 mg/kg, advantageously between about 1.0 and 25 mg/kg.

The analgesic activity can be determined by measuring the potentiation of the analgesic effects of enkephalin and derivatives thereof, and by classical analgesic tests, such as the phenyl-p-benzoquinone induced writing test [J. Pharmacol. Exp. Therap. 125, 237 (1959)] and the hot plate test in the mouse [J. Pharmacol. Exp. Therap. 107, 385 (1953)].

The antihypertensive activity can be determined in the spontaneously hypertensive rat, Goldblatt rat or Goldblatt dog by direct measurement of blood pressure. Advantageously, the effect is measured in the DOCA-salt hypertensive rat and/or renal hypertensive rat or dog model.

The diuretic (saluretic) activity can be determined in standard diuretic screens, e.g. as described in "New Antihypertensive Drugs", Spectrum Publications, 1976, pages 307–321, or by measuring the potentiation of atrial natriuretic factor-induced natriuresis and diuresis in the rate.

The potentiation of ANF can also be determined by measuring the increase in ANF plasma level achieved.

The in vitro inhibition of neutral endopeptidase (NEP) 3.4.24.11 can be determined as follows:

Neutral endopeptidase 3.4.24.11 activity is determined by the hydrolysis of the substrate glutaryl-Ala-Ala-Phe-2-naphthylamide (GAAP) using a modified procedure of Orlowski and Wilk (1981). The incubation mixture (total volume 125 μl) contains 4.2 μg of protein (rat kidney cortex membranes prepared by method of Maeda et al, 1983), 50 mM tris buffer, pH 7.4 at 25° C., 500 μM substrate (final concentration), and leucine aminopeptidase M (2.5 μg). The mixture is incubated for 10 minutes at 25° C. and 100 μl of fast garnet (250 μg fast garnet/ml of 10% Tween 20 in 1M sodium acetate, pH 4.2) is added. Enzyme activity is measured spectrophotometrically at 540 nm. One unit of NEP 24.11 activity is defined as 1 nmol of 2-naphthylamine released per minute at 25° C. at pH 7.4. $IC_{50}$ values are determined, i.e. the concentration of test compound required for 50% inhibition of the release of 2-naphthylamine.

Neutral endopeptidase activity is also determined using ANF as a substrate. Atrial natriuretic factor degrading activity is determined by measuring the disappearance of rat-ANF (r-ANF) using a 3 minute reverse phase-HPLC separation. An aliquot of the enzyme in 50 mM Tris HCl buffer, pH 7.4, is preincubated at 37° C. for 2 minutes and the reaction is initiated by the addition of 4 nmol of r-ANF in a total volume of 50 μl. The reaction is terminated after 4 minutes with the addition of 30 μl of 0.27% trifluoroacetic acid (TFA). Forty microliters of the mixture is injected into a reverse phase-HPLC and analyzed using a C4 cartridge in a 3 minute, isocratic separation. Twenty-three percent of buffer B (0.1% TFA in 80% acetonitrile) is used. Buffer A is 0.1% TFA in water. One unit of activity is defined as the hydrolysis of 1 nmol of r-ANF per minute at 37° C. at pH 7.4. $IC_{50}$ values are determined, i.e. the concentration of test compound required for 50% inhibition of the hydrolysis of ANF.

The test compound is dissolved in dimethyl sulfoxide or 0.25M sodium bicarbonate solution, and the solution is diluted with pH 7.4 buffer to the desired concentration.

In vitro testing is most appropriate for the free phosphono/carboxylic acids of the invention.

Illustrative of the invention, N-[2-(phosphonomethylamino)-3-(4-biphenylyl)-propionyl]-3-aminopropionic acid demonstrates an $IC_{50}$ of about 4.3 nM in the GAAP in vitro assay; the corresponding (S)-antipode has $IC_{50}$ of about 1.6 nM. Similar values are obtained in the rat-ANF in vitro assay.

The effect of the compounds of the invention on rat plasma ANF concentration can be determined as follows:

Male Sprague-Dawley rats (275–390 g) are anesthetized with ketamine (150 mg/kg)/acepromazine (10%) and instrumented with catheters in the femoral artery and vein to obtain blood samples and infuse ANF, respectively. The rats are tethered with a swivel system and are allowed to recover for 24 hours before being studied in the conscious, unrestrained state.

In this assay, plasma ANF levels are determined in the presence and absence of NEP inhibition. On the day of study, all rats are infused continuously with ANF at 450 ng/kg/min. i.v. for the entire 5 hours of the experiment. Sixty minutes after beginning the infusion, blood samples for baseline ANF measurements are obtained (time 0) and the rats are then randomly divided into groups treated with the test compound or vehicle. Additional blood samples are taken 30, 60, 120, 180 and 240 minutes after administration of the test compound.

Plasma concentrations are determined by a specific radioimmunoassay. The plasma is diluted ($\times 12.52$, $\times 25$ and $\times 50$) in buffer containing: 50 mM Tris (pH 6.8), 154 mM NaCl, 0.3% bovine serum albumin, 0.01% EDTA. One hundred microliters of standards [rANF (99–126)] or samples are added to 100 μl of rabbit anti-rANF serum and incubated at 4° C. for 16 hours. Ten thousand cpm of [$^{125}$I]rANF are then added to the reaction mixture which is incubated at 4° C. for an additional 24 hours. Goat anti-rabbit IgG serum coupled to paramagnetic particles is added to the reaction mixture and bound [$^{125}$I]rANF is pelleted by exposing the mixture to an attracting magnetic rack. The supernatant is decanted and the pellets counted in a gamma counter. All determinations are performed in duplicate. Plasma ANF levels are expressed as a percent of those measured in vehicle-treated animals which received ANF along (450 ng/kg/min i.v.).

Illustrative of the invention, (S)-N-[2-(diphenylphosphonomethylamino)-3-(4-biphenylyl)-propionyl]-3-aminopropionic acid at doses of about 1–30 mg/kg p.o., administered in 10% ethanol/polyethylene glycol 400, produces significant increases in plasma ANF levels.

The antihypertensive effect can be determined in desoxycorticosterone acetate (DOCA)-salt hypertensive rats.

DOCA-salt hypertensive rats (280–380 g) are prepared by the standard method. Rats underwent a unilateral nephrectomy and one week later are implanted with silastic pellets containing 100 mg/kg of DOCA. The rats are maintained on 1% NaCl/0.2% KCl drinking water for three to five weeks until sustained hypertension is established. The antihypertensive activity is evaluated at this time.

Two days before an experiment, the rats are anesthetized with methoxyflurane and instrumented with catheters in the femoral artery to measure arterial blood pressure. Forty-eight hours later, baseline arterial pressure and heart rate are recorded during a 1 hour period. The test compound (30 mg/kg p.o.) or vehicle is then administered and the same cardiovascular parameters are monitored for an additional 5 hours.

Illustrative of the invention, (S)-N-[2-(diphenylphosphonomethylamino)-3-(4-biphenylyl)-propionyl]-3-aminopropionic acid at a dose of 30 mg/kg p.o., administered in PEG 400, produces a significant reduction in blood pressure in the DOCA-salt hypertensive rat model.

The potentiation of the natriuretic effect of ANF can be determined as follows:

Male Sprague-Dawley rats (280-360 g) are anesthetized with Inactin (100 mg/kg i.p.) and instrumented with catheters in the femoral artery, femoral vein and urinary bladder to measure arterial pressure, administer ANF and collect urine, respectively. A continuous infusion of normal saline (33 μl/min) is maintained throughout the experiment to promote diuresis and sodium excretion. The experimental protocol consists of an initial 15 minute collection period (designated as pre-control) followed by three additional collection periods. Immediately after completion of the pre-control period, test compound or vehicle is administered; nothing is done for the next 45 minutes. Then, blood pressure and renal measurements are obtained during a second collection period (designated control; 15 min). At the conclusion of this period, ANF is administered (1 μg/kg i.v. bolus) to all animals and arterial pressure and renal parameters are determined during two consecutive 15 minutes collection periods.

Mean arterial pressure, urine flow and urinary sodium excretion are determined for all collection periods. Blood pressure is measured with a Gould p50 pressure transducer, urine flow is determined gravimetrically, sodium concentration is measured by flame photometry, and urinary sodium excretion is calculated as the product of urine flow and urine sodium concentration.

Illustrative of the invention, (S)-N-[2-(diphenylphosphonomethylamino)-3-(4-biphenylyl)-propionyl]-3-aminopropionic acid at a dose of 30 mg/Kg in polyethylene glycol 400 administered intraduodenally produces a significant potentiation of ANF-induced natriuresis.

The compounds of the invention are thus particularly useful as inhibitors of neutral endopeptidase, enhancing the potency and duration of action of atrial natriuretic peptide(s). The compounds are therefore particularly useful for the treatment of cardiovascular disorders such as hypertension, edema and salt retention, and cardiac conditions such as congestive heart failure.

The compounds of the invention can be prepared using processes described and illustrated below for compounds depicted by formula II wherein $R_1$ is located at the para position. Such processes comprise:

(a) condensing a compound of the formula IV

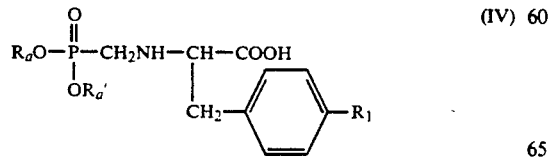

or a reactive carboxy functional derivative thereof wherein $R_a$ and $R_a'$ represent lower alkyl or aryl-lower alkyl, e.g. optionally substituted benzyl (as phosphonyl hydroxy protecting groups) and $R_1$ has meaning as defined herein; with a compound of the formula V

wherein $COR_3$ represents esterified carboxyl and A, $R_2$ and m have meaning as defined hereinabove; or (b) reacting a compound of formula VI

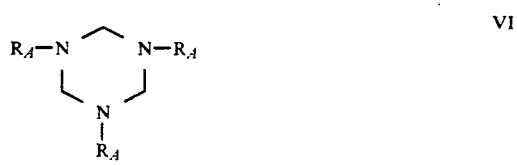

wherein $R_A$ represents the grouping

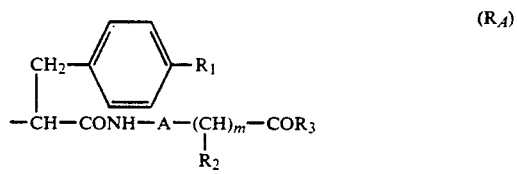

wherein $R_1$, A, m and $R_2$ have meaning as defined above, and $COR_3$ represents esterified carboxyl; with a diester of phosphonic (phosphorous) acid, also named as a disubstituted phosphite, of formula VII

wherein $R_b$ and $R_b'$ have meaning as defined herein for R and R' in formula II, except that $R_b$ and $R_b'$ do not represent hydrogen, and $R_b$ and $R_b'$ may in addition represent lower alkyl or aryl-lower alkyl; or (c) reacting a compound of formula VIII

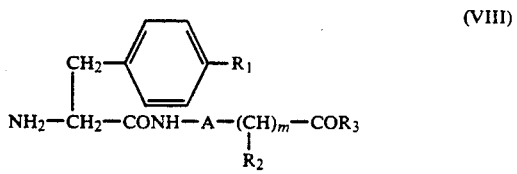

wherein $COR_3$ represents esterified carboxyl and $R_1$, $R_2$, A and m have meaning as defined above, with a reactive esterified derivative of a hydroxymethylphosphonic acid derivative of the formula IX

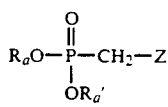

(IX)

wherein $R_a$ and $R_a'$ represent lower alkyl or aryl-lower alkyl, e.g. optionally substituted benzyl, and Z represents a leaving group, e.g. a reactive esterified hydroxyl group, such as trifluoromethylsulfonyloxy;
and in above said processes, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic or phosphonic acid function into a pharmaceutically acceptable ester or amide derivative, or converting a resulting ester or amide into the free acid or into another ester or amide derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

In starting compounds and intermediates which are converted to the compounds of the invention in a manner described herein, functional groups present, such as phosphonyl, carboxyl, amino and hydroxy groups, are optionally protected by conventional protecting groups that are common in preparative organic chemistry. Protected phosphonyl, carboxyl, amino and hydroxy groups are those that can be converted under mild conditions into free phosphonyl, carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (phosphonyl, carboxyl group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene, "Protective Groups in Organic Synthesis", Wiley, N.Y. 1984, and also in "The Peptides", Vol. I, Schroeder and Luebke, Academic Press, London, N.Y., 1965.

The preparation of compounds of the invention according to process (a), i.e. the condensation of an amine of formula V with the acid of formula IV, or a functional reactive derivative thereof, is carried out by methodology well-known for peptide synthesis.

Reactive functional derivatives of compounds of formula IV are preferably halides, mixed anhydrides such as the pivaloyl, alkoxycarbonyl or cyanoacetyl anhydride.

The condensation of an amino ester of formula V with a free carboxylic acid of formula IV is carried out advantageously in the presence of a condensing agent such as dicyclohexylcarbodiimide or N-(3-dimethylaminopropyl)-N'-ethylcarbodiimide and hydroxybenzotriazole in an inert polar solvent such as dimethylformamide or methylene chloride, preferably at room temperature.

The condensation of an amino ester of formula V with a reactive functional derivative of an acid of formula IV in the form of an acid halide, advantageously an acid chloride, or mixed anhydride, is carried out in an inert solvent such as toluene or methylene chloride, advantageously in the presence of a base, e.g. an inorganic base such as potassium carbonate or an organic base such as triethylamine or pyridine, preferably at room temperature.

A resulting compound of formula IIb

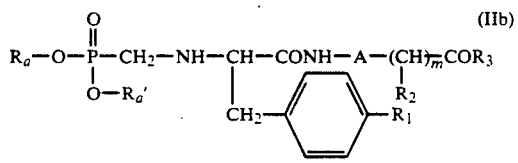

(IIb)

wherein $R_1$, $R_2$, $COR_3$, A and m have meaning as defined above and wherein $R_a$ and $R_a'$ represent lower alkyl or aryl-lower alkyl can be converted to a compound of formula II wherein R and R' represent hydrogen, using known reagents for converting phosphonic acid esters to phosphonic acids, e.g. hydrobromic acid in glacial acetic acid, trimethylsilyl bromide, or by catalytic hydrogenation when $R_a$ and $R_a'$ represent optionally substituted benzyl.

Starting materials of formula IV can be converted to the corresponding reactive functional derivative, e.g. an acyl halide, by treatment with e.g. oxalyl chloride in methylene chloride.

The starting materials of formula V are various amino acid ester derivatives known in the art or which may be prepared by conventional methods known in the art.

The starting materials of formula IV may be prepared according to methods described herein, e.g. in particular those illustrated by the examples herein.

One method for the preparation of the starting materials of formula IV involves the reductive amination of the appropriate biarylpyruvic acid or derivative thereof with a diester of aminomethylphosphonic acid (e.g. the dimethyl ester), in the presence of a reducing agent such as hydrogen or sodium cyanoborohydride under standard reductive amination conditions, e.g. as illustrated in the examples.

The aminomethylphosphonic acid diesters used are prepared according to methods known in the art, for instance by reaction of phthalimidomethyl bromide with trimethylphosphite [P(OCH$_3$)$_3$] to obtain the corresponding dimethyl phthalimidomethyl phosphonate which is converted with hydrazine to dimethyl aminomethylphosphonate.

As to the biarylpyruvic acids, such are known in the art or are in turn prepared by methods analogous to those used for the preparation of substituted pyruvic acids, e.g. by condensation of the biarylmethyl halide with an appropriately protected glyoxalic acid derivative, or by condensation of the e.g. methyl ester of a biarylacetic acid with diethyl oxalate in the presence of a base, e.g. potassium t-butoxide, followed by hydrolytic decarboxylation.

An alternate method for the preparation of the starting materials of formula IV involves the condensation of e.g. a lower alkyl or aryl-lower alkyl ester of the biarylalanine with a reactive esterified derivative of hydroxymethylphosphonic acid of formula IX, e.g. dimethyl (trifluoromethylsulfonyloxy)-methylphosphonate (prepared e.g. according to Organic Synthesis 64, 80 (1985) and Tetrahedron Letters 1986, 1477) in a polar solvent, such as methylene chloride, in the presence of a base, e.g. a tertiary amine such as diisopropylethylamine, at a temperature near room temperature. The resulting carboxylic acid ester is selectively hydrolyzed to the carboxylic acid according to methods for carboxylic acid ester hydrolysis well known in the art.

Biarylalanines are either known in the art or can be prepared according to methods reported in the art.

As to the preparation of the biarylalanines as starting materials in optically active form, such can be prepared e.g. by resolution or by one of the following methods:

(a) Adapting a method described in Tetrahedron Letters 1988, 6075, a biarylmethanol, e.g. 4-biphenylylmethanol, is converted to a reactive derivative, e.g. the bromide, which is then condensed with an N-acyl derivative of 2,3-diphenyl-6-oxomorpholine, e.g. the N-carbobenzyloxy-(2R,3S)-isomer, in the presence of a strong base such as sodium bis-trimethylsilylamide, to yield e.g. N-carbobenzyloxy-2(R), 3(S), 5(S)-6-oxo-2,3-diphenyl-5-(4-biphenylylmethyl)morpholine. Catalytic hydrogenolysis, e.g. using hydrogen and palladium on charcoal as catalyst, yields the optically active (S)-(+)-4-biphenylalanine.

(b) Alternatively, using the Pd (0)-catalyzed cross-coupling reaction described in Tetrahedron Letters 31, 1665 (1990), J. Organic Chemistry 55, 906 (1990) and Tetrahedron 45, 6670 (1989) as developed by W. Shieh et al, the substantially optically pure chiral biarylalanines, of the formula

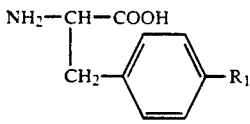

or the N-acyl and/or carboxy ester derivatives thereof wherein $R_1$ has meaning as defined hereinabove, can be prepared by: condensing a reactive esterified optically active tyrosine derivative of the formula

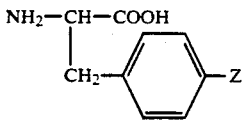

wherein the amino and carboxy groups are in protected form (as N-acyl and esterified carboxy ester derivatives), and Z represents reactive esterified hydroxy (advantageously trifluoromethylsulfonyloxy) with an aryl boronic acid in which aryl corresponds to $R_1$ as defined above, in the presence of a palladium (0) catalyst, in particular tetrakis(triphenylphosphine)palladium (0), and in the presence of an anhydrous base (such as an alkali metal carbonate), in an inert solvent (such as xylene or toluene) at an elevated temperature ranging from about 50° to 150° C., and removing any protecting groups as required.

For example, N-t-butoxycarbonyl-tyrosine methyl ester is first converted to N-t-butoxycarbonyl-4-trifluoromethylsulfonyloxy-phenylalanine methyl ester (N-t-butoxycarbonyltyrosine triflate methyl ester). This compound is then condensed with an arylboronic acid (e.g. phenylboronic acid) in the presence of anhydrous potassium carbonate, and tetrakis (triphenylphosphine) palladium (0) complex as catalyst, in toluene preferably at an elevated temperature, advantageously at about 100° to obtain N-t-butoxycarbonyl-4-biphenylalanine methyl ester. After N-deacylation, substantially optically pure 4-biphenylalanine methyl ester is obtained with a configuration corresponding to that of the tyrosine derivative used as starting material.

The arylboronic acids are either commercial or can be prepared as described in the literature, e.g. J. Org. Chem. 49, 5237 (1984).

The preparation of compounds of the invention according to process (b), i.e. the condensation of a hexahydrotriazine derivative of formula VI with a phosphonic acid diester of formula VII (which process is similar to the process illustrated in U.S. Pat. No. 4,053,505 for the preparation of N-phosphonomethylglycine) is carried out in an inert solvent such as toluene or benzene, preferably at elevated temperature, to yield e.g. a compound of formula IIc

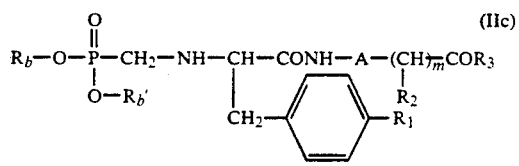

wherein A, m, $R_1$, $R_2$, $COR_3$, $R_b$ and $R_b'$ have meaning as defined above.

A resulting compound of formula IIc wherein $R_b$ and $R_b'$ represent lower alkyl or aryl-lower alkyl can be converted to a compound of formula II wherein R and R' represent hydrogen, using known reagents for converting phosphonic acid esters to phosphonic acids, e.g. hydrobromic acid in glacial acetic acid, trimethylsilyl bromide, or by catalytic hydrogenation provided that $R_b$ and $R_b'$ represent optionally substituted benzyl.

The phosphonic acid (phosphite) diesters of formula VII are known or can be prepared according to methods in the literature, e.g. U.S. Pat. No. 3,329,742 for the preparation of diaryl phosphites.

Unsymmetrical phosphonic acid diesters can be prepared by first treating a symmetrical diester, e.g. dibenzyl phosphite, with aqueous base, e.g. aqueous tetramethyl ammonium hydroxide, to obtain a monoester, e.g. monobenzyl phosphite. This can be treated e.g. with an appropriate alkyl halide corresponding to R or R' in formula II, for example an α-acyloxyalkyl bromide, to obtain a compound of formula VII wherein $R_b$ is benzyl and $R_b'$ is α-acyloxyalkyl. Alternatively, monobenzyl phosphite can first be converted to e.g. a mixed anhydride (e.g. with pivaloyl chloride) which is then reacted with an appropriate alcohol or phenol corresponding to R or R' in formula II to obtain a corresponding unsymmetrical diester of formula VII. The resulting condensation product of formula IIc wherein either $R_b$ or $R_b'$ represents benzyl can then be converted to a compound of formula II wherein either R or R' represents hydrogen by selective catalytic hydrogenolysis of the benzyl substituent.

As to the hexahydrotriazines of formula VI, such can be prepared as follows:

An N-acylbiarylalanine ester, e.g. N-t-butoxycarbonyl-4-biphenylalanine methyl ester, prepared as described herein, is selectively hydrolyzed with dilute base to the corresponding N-acylbiarylalanine, e.g. N-t-butoxycarbonyl-4-biphenylalanine. The carboxylic acid is condensed with an amino acid ester of formula V under standard conditions of peptide synthesis, e.g. as described under process (a) herein, to obtain a compound of formula VIII (which is the amino substituted radical $R_A$ in formula VI)

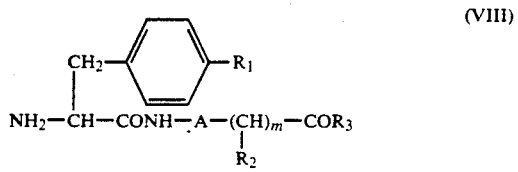

(VIII)

wherein $COR_3$ represents esterified carboxyl, and $R_1$, $R_2$, A and m have meaning as defined above.

Condensation of an ester of formula VIII, according to the general known process for the synthesis of hexahydrotriazine derivatives, e.g. as described in J. Org. Chem. 53, 3113 (1988), with formaldehyde, preferably 37% aqueous formaldehyde, advantageously in a solvent such as a mixture of ethyl acetate and water at room temperature, yields a corresponding hexahydrotriazine derivative of formula VI.

The preparation of compounds of the invention according to process (c) is carried out essentially as described above for the preparation of a compound of formula IV above and the starting materials are also prepared according to methods described herein.

Compounds of the invention wherein $COR_3$ represents carboxyl derivatized in form of a pharmaceutically acceptable amide can also be prepared according to the above methods using corresponding starting materials wherein $COR_3$ represents carbamoyl or N-substituted carbamoyl.

The compounds of the invention so obtained, can be converted into each other according to conventional methods. Thus, for example, resulting amides or esters may be hydrolyzed with aqueous alkalies, such as alkali metal carbonates or hydroxides. Resulting free acids may be esterified with e.g. said unsubstituted or substituted alkanols or reactive esterified derivatives thereof such as alkyl halides, or diazoalkanes. Free acids are also converted into said metal, ammonium or acid addition salts in conventional manner.

Thus, any resulting free acid or base can be converted into a corresponding metal, ammonium or acid addition salt respectively, by reacting it with an equivalent amount of the corresponding base, basic salt, acid or ion exchange preparation, e.g. said free acids with alkali or ammonium hydroxides or carbonates, or e.g. free amines with said inorganic or organic acids respectively. Any resulting salt may also be converted into the free compound, by liberating the latter with stronger acids or bases, respectively. In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization. Furthermore, the functional derivatives of the free acids of formula I, wherein either the phosphono and/or carboxy groups are esterified by identical or different radicals may be prepared by condensing a free acid of formula I or a mono- or di-ester derivative thereof with an esterifying agent of the formula X

$$R_5-Z \qquad (X)$$

wherein Z represents hydroxy or a reactive esterified hydroxyl group; and $R_5$ represents an esterifying radical as defined herein for the phosphonyl esters (e.g. R and R') and the carboxylic esters (encompassed e.g. by $COR_3$ representing esterified carboxy), in particular said non-aromatic radicals.

A reactive esterified hydroxyl group, such as Z in a compound of the formula IX or X, is a hydroxyl group esterified by a strong inorganic or organic acid. Corresponding Z groups are in particular halo, for example chloro, bromo or preferably iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The esterification of the carboxyl or phosphonyl groups, optionally in salt form, with a compound of formula X wherein Z represents a reactive esterified hydroxyl group, is performed in a manner known per se, in the presence of for example an organic base, such as an organic amine, for example a tertiary amine, such as tri-lower alkylamine, for example trimethylamine, triethylamine or ethyl-di-isopropylamine, an N,N-di-lower-alkyl-aniline, for example N,N-di-methylaniline, a cyclic tertiary amine, such as an N-lower-alkylated morpholine, for example N-methyl-morpholine, a base of the pyridine type, for example pyridine, an inorganic base, for example hydroxides, carbonates, or hydrogen carbonates of alkali metals or alkaline-earth metals, for example sodium, potassium or calcium hydroxide, carbonate or hydrogen carbonate, or a quaternary ammonium base, such as a tetraalkylammonium hydroxide, carbonate or hydrogen carbonate, for example in which alkyl is e.g. methyl, ethyl, propyl, isopropyl, butyl, or the like, or an alkali metal salt of bis-trialkylsilylamide (e.g. trimethyl) optionally in the presence of a crown ether such as 18-crown-6 in a suitable inert solvent or solvent mixture, e.g. acetonitrile, toluene, and the like.

A trifunctional free acid, e.g. of the formula I, or a monoester or diester thereof, is preferably first converted into a salt of one of the stated organic or inorganic bases, especially into the sodium or potassium salt, and is then reacted with a compound of the formula X. The compounds of formula X are known or can be prepared by methods well-known to the art.

A compound of the formula or X wherein Z is a reactive esterified hydroxyl group can be prepared in situ. For example, a compound of the formula X wherein Z is chloro can be converted by treatment with sodium iodide in a solvent, for example in acetone or acetonitrile, into a compound of the formula X wherein Z is iodo; or esterification can be carried out with a chloro compound of the formula X in the presence of sodium iodide.

Esterification of a compound with a free carboxyl group using in excess an alcohol of formula X (wherein Z represents hydroxy) is carried out in a manner known per se, e.g. in the presence of an acid catalyst e.g. sulfuric acid or boron trifluoride etherate, preferably at an elevated temperature, advantageously ranging from about 40° C. to 100° C. Alternately, the esterification of a compound with a free carboxyl group can be carried out with at least an equimolar amount of the alcohol in the presence of a condensing agent such as dicyclohexylcarbodiimide or N-(3-dimethylaminopropyl)-N'-ethylcarbodiimide in a polar solvent such as methylene chloride, in the presence of a base if required, e.g. such as 4-(dimethylamino)pyridine.

Conversely, esters of the invention, phosphonic acid or carboxylic acid esters, can be converted to compounds of the invention with a free carboxy and/or one or two free phosphonyl hydroxy groups using methods and conditions generally known in the art and illustrated herein. Depending on type of ester involved, useful reagents include aqueous acids or bases; also anhydrous reagents such as trialkylsilyl halides, hydrobromic acid in glacial acetic acid; also hydrogen and a hydrogenolysis catalyst. For instance, trialkyl esters can be converted to the free trifunctional acids by treatment with hydrobromic acid in glacial acetic acid, e.g. at room temperature or elevated temperature. Also trialkyl esters can be converted to the mono esters wherein carboxy only remains esterified, by treatment with e.g. trimethylsilyl bromide at room temperature.

Any benzyl esters can be selectively hydrogenolyzed with e.g. hydrogen in the presence of a catalyst such as palladium on charcoal.

Phosphono diesters wherein the esterifying groups (R and R') represent α-acyloxyalkyl (for instance the compounds of formula IIIa) can be converted to corresponding phosphono monoesters (wherein one of R and R' represents hydrogen) by treatment with one molar equivalent of an aqueous base, e.g. 1N sodium hydroxide.

Phosphono diesters wherein the esterifying groups (e.g. R and R' in formula II) represent aryl (for instance the compounds of formula IIIc) can advantageously be converted to the corresponding phosphono monoesters (wherein one of R and R' represents hydrogen) using dilute aqueous acid (e.g. dilute hydrochloric acid) in a polar water miscible solvent such as acetonitrile.

Furthermore, phosphono diesters wherein the esterifying groups represent aryl can first be converted to the corresponding phosphono diesters wherein the esterifying groups represent e.g. methyl, by treatment with methanol in the presence of potassium fluoride and a crown ether such as 18-crown-6. Subsequent treatment with hydrobromic acid in glacial acetic acid yields the free phosphonic acid.

In the case mixtures of stereoisomers or optical isomers of the above compounds are obtained, these can be separated into the single isomers by methods in themselves known, e.g., by fractional distillation, crystallization and/or chromatography. Racemic products can be resolved into the optical antipodes, for example, by separation of diastereomeric salts thereof, e.g., for basic compounds by the fractional crystallization of d- or l-(tartrate, mandelate or camphorsulfonate) salts, or for acidic compounds by fractional crystallization of d- or l-(alpha-methylbenzylamine, cinchonidine, cinchonine, quinine, quinidine, ephedrine, dehydroabietylamine, brucine or strychnine)-salts.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, e.g. as neutral endopeptidase inhibitors, e.g. for the treatment of cardiovascular disorders such as hypertension, edema, salt retention and congestive heart failure.

The present invention also relates to the use of the compounds of the invention for the preparation of pharmaceutical compositions especially pharmaceutical compositions having neutral endopeptidase inhibiting activity, and e.g. antihypertensive or saluretic activity.

The pharmaceutical compositions according to the invention are those suitable for enteral, such as oral or rectal, transdermal and parenteral administration to mammals, including man, for the treatment of cardiovascular disorders, such as hypertension, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 10 and 100 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium), 365 nm (mercury lamp with filter) or other wavelengths as specified in the examples.

The prefixes R and S are used to indicate the absolute configuration at each asymmetric center.

EXAMPLE 1 a) A solution of t-butyl N-[2-(dimethylphosphonomethylamino)-3-(4-biphenylyl)-propionyl]-3-aminopropionate (0.38 g, 0.78 mmol) in 30% HBr/glacial HOAc is stirred at room temperature for 6.5 hours. After concentration to about 1/10 volume, ether (40 mL) is added and the solid filtered. The solid is then suspended in water (3 mL), filtered off and washed with water to obtain N-[2-(phosphonomethylamino)-3-(4-biphenylyl)-propionyl]-3-aminopropionic acid, m.p. 242°-244° dec.

The starting material is prepared as follows:

A mixture of dimethyl phthalimidomethylphosphonate (15 g, 56 mmol), hydrazine (99%, 2.2 mL, 69.3 mmol) and methanol (225 mL) is stirred at room temperature for 18 hours. The suspension is then heated to reflux for 4 hours, cooled to room temperature, filtered and the solid washed with toluene. The filtrate is evaporated to ca ⅓ volume and then decanted from some additional solid material. Removal of the solvent yields aminomethylphosphonic acid dimethyl ester as a colorless oil.

To a stirred suspension of 4-biphenylyl-pyruvic acid in anhydrous THF-EtOH (50 mL, 9:1) is added aminomethylphosphonic acid dimethyl ester (520 mg, 3.7 mmol) in THF-EtOH (5 mL, 9:1). The pH is then adjusted with triethylamine to 6.6. After 20 minutes, sodium cyanoborohydride (100 mg, 1.6 mmol) in THF (2.5 mL) is added over 30 minutes. The solution is stirred for 18 hours and then concentrated. Ether (20 mL) is added and the mixture is cooled and treated with 1N HCl (7 mL). After stirring at room temperature for 30 minutes, the solid is filtered off and washed with ether and water to yield 2-(dimethylphosphonomethylamino)-3-(4-biphenylyl)-propionic acid as a waxy solid.

A solution of 2-(dimethylphosphonomethylamino)-3-(4-biphenylyl)-propionic acid (2.27 g, 6.25 mmol), β-alanine t-butyl ester hydrochloride (1.36 g, 7.5 mmol), hydroxybenzotriazole (1.05 g, 6.85 mmol), triethylamine (2.41 mL, 17.3 mmol) and 1-(3-dimethylaminopropyl)-3-ethylcarbodiimide hydrochloride (EDC, 1.6 g, 8.22 mmol) in dimethylformamide (60 mL) is stirred for 3 hours at room temperature, then diluted with ethyl acetate, washed with ice water, dried ($Na_2SO_4$) and chromatographed on silica gel [$CH_2Cl_2$:MeOH:hexanes/76:4:20] to obtain t-butyl N-[2-(dimethylphosphonomethylamino)-3-(4-biphenylyl)-propionyl]-3-aminopropionate.

EXAMPLE 2

A solution of t-butyl S-(+)-N-[2-(dimethylphosphonomethylamino)-3-(4-biphenylyl)-propionyl]-3-aminopropionate (0.4 g, 0.83 mmol) and 30% HBr/glacial HOAc (9 mL) is stirred at room temperature. After 6.5 hours the solution is concentrated and treated with ether (80 mL). The resulting white solid is filtered, washed with water and ether, and dried under vacuum to yield S-(+)-N-[2-(phosphonomethylamino)-3-(4-biphenylyl)-propionyl]-3-aminopropionic acid, m.p. 251°-2° dec., $[\alpha]_D^{25} = +21.73°$ (c=0.64, water containing 2 mole equivalents sodium hydroxide).

The starting material is prepared as follows:

A suspension of 4-biphenylmethanol (62.9 g, 340 mmol) in hexane (650 mL) is treated with phosphorus tribromide (16 mL, 171 mmol) dropwise over 10 minutes. After 20 minutes $CH_2Cl_2$ (200 mL) is added to dissolve the remaining solid. The solution is then stirred for 1.5 hours and treated with water (200 mL) and then ethyl acetate. The organic layer is washed with water, cold saturated sodium bicarbonate and water, dried over sodium sulfate and evaporated to dryness to yield 4-biphenylmethyl bromide, m.p. 79°-80° C.

The above bromide (29 g, 117 mole) and N-carbobenzyloxy-(2R,3S)-(−)-6-oxo-2,3-diphenyl-morpholine (15 g, 39 mmol) are dissolved in THF (1 L), cooled to −78° and treated with sodium bis-trimethylsilylamide (39 mL, 39 mmol) dropwise over 6-7 minutes. After 20 minutes the bath is removed and the reaction allowed to warm slowly to room temperature. After 3 hours the reaction is poured over 500 mL of ice water and extracted with ethyl acetate. The organic layer is washed with brine, dried over sodium sulfate, concentrated and chromatographed on silica gel (1:1 hexanes:methylene chloride) to yield N-carbobenzyloxy-2(R), 3(S), 5(S)-6-oxo-2,3-diphenyl-5-(4-biphenylmethyl)-morpholine, m.p. 151°-52°.

A mixture of N-carbobenzyloxy-2(R), 3(S), 5(S)-6-oxo-2,3-diphenyl-5-(4-biphenylylmethyl)-morpholine (10 g, 18.0 mmol), methanol (400 mL), THF (200 mL) and 10% Pd/C (10 g) is hydrogenated in a Parr apparatus. After 8 hours, the catalyst is filtered off, washed with 2N HCl (15 mL) then with methanol (150 mL). The filtrate is concentrated to dryness to give a solid residue. After trituration with ether, S-(+)-(4-biphenyl)alanine hydrochloride is obtained as a crystalline solid; m.p. 257° C. (dec.), $[\alpha]^{23}_{365} = +11.36°$ (c=0.827, $CH_3OH$).

S-(+)-(4-biphenyl)alanine hydrochloride (3.2 g, 11 mmol) is refluxed in methanol (75 mL) in the presence of hydrochloric acid gas for 1 hour. Dilution with ether (100 mL) precipitates S-(+)-(4-biphenyl)alanine hydrochloride methyl ester as a crystalline solid; m.p. 220°-221° C., $[\alpha]^{25}_D = +12.8°$ (c=0.68, $CH_3OH$).

S-(+)-(4-biphenyl)-alanine methyl ester can also be prepared as follows:

A solution of α-t-BOC-(S)-tyrosine methyl ester (5.9 g, 20 mmol) and pyridine (8 mL, 100 mmol) in methylene chloride (30 mL) is cooled to 0°–5°. Trifluoromethanesulfonic anhydride (4 mL, 23 mmol) is added at 0°–5°, and the resulting mixture is held for another 30 minutes. The reaction mixture is diluted with water (60 mL) and methylene chloride (100 mL), and washed sequentially with 0.5 N sodium hydroxide solution (1×50 mL), water (1×60 mL), 10% citric acid solution (2×75 mL) and water (1×60 mL). The organic phase is dried over MgSO$_4$ and concentrated to an oil. The oil is purified by column chromatography (silica gel, hexane/ethyl acetate, 2:1 to give methyl(S)-2-(t-butoxycarbonylamino)-3-[4-(trifluoromethylsulfonyloxy)-phenyl]-propionate which crystallizes on standing; m.p. 47°–48°; $[\alpha]^{20}_D$+33.6° (c=1, CHCl$_3$).

Nitrogen is passed through a suspension of (S)-2-(t-butoxycarbonylamino)-3-[4-(trifluoromethylsulfonyloxy)-phenyl]-propionate (1.75 mmol), phenylboronic acid (3.5 mmol), anhydrous potassium carbonate (2.63 mmol) and toluene (17 mL) for 15 minutes. Tetrakis(triphenylphosphine)palladium(0) is added, and the mixture is heated at 85°–90° for 3 hours. The reaction mixture is cooled to 25°, diluted with ethyl acetate (17 mL) and washed sequentially with saturated sodium bicarbonate (1×20 mL), water (1×20 mL), 10% citric acid (1×20 mL), water (1×20 mL) and saturated sodium chloride solution (1×20 mL). The organic phase is concentrated, and the residue is purified by column chromatography (silica gel, hexane/ethyl acetate 2:1) to yield methyl (S)-2-(t-butoxycarbonylamino)-3-(4-biphenylyl)-propionate which can also be called N-(S)-t-butoxycarbonyl-(4-biphenyl)-alanine methyl ester, m.p. 83°–85°; $[\alpha]^{20}_D$+54.81° (c=1, CHCl$_3$).

To a solution of methyl (S)-2-(t-butoxycarbonylamino)-3-(4-biphenylyl)-propionate (1.25 mmol) in ethyl acetate (2 mL), is added a saturated solution of anhydrous hydrogen chloride in ethyl acetate (4.5 mL). The solution is stirred at room temperature for 3 hours. The reaction mixture is concentrated to obtain methyl (S)-2-amino-3-(4-biphenylyl)-propionate hydrochloride, m.p. 205°–207°; [60 ]$_D^{20}$+11.8° (c=1, CH$_3$OH), also named (S)-(4-biphenyl)-alanine methyl ester hydrochloride.

Similarly prepared are also the following biaryl alanine methyl esters:
(1) methyl (S)-2-amino-3-(4'-methyl-4-biphenylyl)-propionate hydrochloride, m.p. 207° (dec); $[\alpha]^{20}_D$+11.83° (c=1, CH$_3$OH);
(2) methyl (S)-2-amino-3-(4'-chloro-4-biphenylyl)-propionate hydrochloride, m.p. 206°–208°; $[\alpha]^{20}_D$+12.80° (c=1, CH$_3$OH);
(3) methyl (S)-2-amino-3-[4-(2-furanyl)-phenyl]-propionate hydrochloride, m.p. 207°–208°; $[\alpha]^{20}_D$+16.36° (c=1, CH$_3$OH); and
(4) methyl (S)-2-amino-3-[4-(2-thienyl)phenyl]-propionate hydrochloride.

To a mixture of (S)-(4-biphenyl)alanine methyl ester (2.2 g, 7.8 mmol), methylene chloride (15 ml) and diisopropylethylamine (3 mL, 17.2 mmol) cooled to 0° C., is added a solution of dimethyl (trifluoromethylsulfonyloxy)methylphosphonate (2.32 g, 8.54 mmol, Tetrahedron Letters 1986, 1477) in methylene chloride (16 mL) over 7 minutes. After 2 hours the temperature is raised slowly to room temperature and an additional 1.5 g (5.5 mmol) of the phosphonate ester and diisopropylethyl amine (0.96 mL, 5.5 mmol) is added over 6 hours. After 18 hours the reaction mixture is extracted with sat. NaHCO$_3$ and water. The organic layer is dried with Na$_2$SO$_4$, concentrated and chromatographed on silica gel (EtOAc/hexanes; 9:1) to yield methyl S-(+)-2-(dimethylphosphonomethylamino)-3-(4-biphenylyl)-propionate, $[\alpha]^{25}_{365}$=+39.37° (c=1.044, CH$_3$OH).

A mixture of methyl S-(+)-2-(dimethylphosphonomethylamino)-3-(4biphenylyl)-propionate (1.621 g, 4.3 mmol), 1N NaOH (6.44 mL, 6.44 mmol) and methanol (20 mL) is stirred at room temperature for 5 hours. 1N HCl (6.6 mL, 6.6 mmol) is added, the mixture is extracted a few times with methylene chloride, and the combined extracts are dried (MgSO$_4$) and concentrated to yield (S)-2-(dimethylphosphonomethylamino)-3-(4-bihenylyl)-propionic acid, m.p. 133°–6°; $[\alpha]^{25}_D$=+77.34° (c=0.834, CH$_3$OH). The carboxylic acid (1.0 g, 2.75 mmol) is stirred with β-alanine-t-butyl ester (0.60 g, 3.31 mmol), triethylamine (1.07 mL, 7.63 mmol), 1-hydroxybenzotriazole (HOBT, 0.44 g, 2.89 mmol), N-(3-dimethylaminopropyl)-N'-ethylcarbodiimide hydrochloride (EDC, 0.7 g, 3.64 mmol) in DMF (25 mL). After 3 hours the reaction is diluted with EtOAc, washed with water, dried with Na$_2$SO$_4$, concentrated and chromatographed on silica gel [CH$_2$Cl$_2$:MeOH:hexanes/76:4:20] to yield t-butyl S-(+)-N-[2-(dimethylphosphonomethylamino)-3-(4-biphenylyl)-propionyl]-3-aminopropionate, as a colorless oil.

EXAMPLE 3

A solution of ethyl S(+)-N-[2-(dimethylphosphonomethylamino)-3-(4-biphenylyl)-propionyl]-3-aminopropionate (220 mg, 0.48 mmol) in CH$_2$Cl$_2$ (2 mL) is treated with trimethylsilyl bromide (TMSBr, 0.44 g, 2.85 mmol) at room temperature. After 2 hours the solution is concentrated and the residue is treated with water (3 mL) and stirred for 30 minutes. The mixture is filtered and dried to obtain ethyl S(+)-N-[2-(phosphonomethylamino)-3-(4-biphenylyl)-propionyl]-3-aminopropionate, m.p. 251°-2° dec., $[\alpha]^{25}_{365}$=+6.20°, (c=0.802, water containing 2 eq. of NaOH).

The starting material is prepared analogously to the t-butyl ester in example 2.

EXAMPLE 4

Similarly to procedures described in examples 1 and 2 are prepared:
(a) N-[2-(phosphonomethylamino)-3-(4-biphenylyl)-propionyl]-4-aminobutyric acid, m.p. 218°–220° dec.
(b) N-[2-(phosphonomethylamino)-3-(4-biphenylyl)-propionyl]-L-phenylalanine, m.p. 225° dec.
(c) N-[2-(phosphonomethylamino)-3-(4-biphenylyl)propionyl]-glycine, m.p. 232° dec.
(d) N-[2-(phosphonomethylamino)-3-(4-biphenylyl)-propionyl]-7-aminoheptanoic acid;
(e) N-[2-(phosphonomethylamino)-3-(4-biphenylyl)-propionyl]-4-aminocyclohexylcarboxylic acid.

EXAMPLE 5

Similarly to procedures previously described, e.g. in examples 1–3, are prepared:
(a) Benzyl N-[2-(phosphonomethylamino)-3-(4-biphenylyl)-propionyl]-3-aminopropionate, m.p. 258°–260°; also the S-(+) antipode;
(b) n-Decyl N-[2-(phosphonomethylamino)-3-(4-biphenylyl)-propionyl]-3-aminopropionate, m.p. 232°–235°;

(c) Omega-aminopentyl N-[2-(phosphonomethylamino)-3-(4-biphenylyl)-propionyl]-3-aminopropionate hydrobromide, m.p. 230°-232° dec.;

(d) 3-Pyridylmethyl N-[2-(phosphonomethylamino)-3-(4-biphenylyl)-propionyl]-3-aminopropionate hydrochloride, m.p. 218°-220°.

EXAMPLE 6

A solution of ethyl N-[2-(phosphonomethylamino)-3-(4-biphenylyl)-propionyl]-3-aminopropionate (0.3 g, 0.69 mmol), 18 crown-6 (0.36 g, 1.38 mmol) in toluene (12 mL) is cooled to 0° and is treated with potassium bis-trimethylsilylamide (2.22 mL, 1.45 mmol). After 7 minutes the clear solution is treated with iodomethyl pivalate (0.25 mL, 1.56 mmol) and stirred for 18 hours. Ethyl acetate is added, the mixture is washed with water, dried ($Na_2SO_4$), concentrated and the residue is chromatographed on silica gel (EtOAc/hexanes, 75:25) to obtain ethyl N-{2-[di-(pivaloyloxymethyl)-phosphonomethylamino]-3-(4-biphenylyl)propionyl}-3-aminopropionate as an oil.

EXAMPLE 7

A suspension of benzyl S-(+)-N-[2-(phosphonomethylamino)-3-(4-biphenylyl)-propionyl]-3-aminopropionate (1.7 g, 3.44 mmol) in dry chloroform (30 mL) is treated with triethylamine (1.92 mL, 13.75 mmol). α-Propionyloxyisobutyl bromide (1.66 mL, 10.3 mmol, Helv. Chim. Acta 61, 2047, 1978), tetrabutylammonium hydrogen sulfate (0.58 g, 1.72 mmol) and sodium iodide (0.26 g, 1.72 mmol) are added sequentially. The mixture is heated under nitrogen at 65° C. After 14 hours, the solution is poured into ice-water and extracted with ethyl acetate (50 mL). The organic layer is dried over magnesium sulfate. Evaporation under reduced pressure yields an oily residue that is purified by chromatography on silica gel, eluting with a gradient of ethyl acetate in hexane (50% to 100%). Benzyl S-(+)-N-{2-[di-(α-propionyloxyisobutyl)-phosphonomethylamino]-3-(4-biphenylyl)-propionyl}-3-aminopropionate is obtained as an oil.

EXAMPLE 8

Benzyl S-(+)-N-{2-[di-(α-propionyloxyisobutyl)-phosphonomethylamino]-3-(4-biphenylyl)-propionyl}-3-aminopropionate (0.34 g, 0.45 mmol) is dissolved in ethyl acetate (20 mL) and hydrogenated under 3 atmospheres pressure over 10% Pd-C (0.34 g) for 2.5 hours. Filtration of the catalyst through Celite and evaporation of the solvent yields a residue that is chromatographed on silica gel, eluting with methylene chloridemethanol (95:5). S-(+)-N-{2-[di-(α-propionyloxyisobutyl)-phosphonomethylamino]-3-(4-biphenylyl)-propionyl}-3-aminopropionic acid is obtained as an oil.

EXAMPLE 9

Similarly to procedures previously described, e.g. in examples 6-8, the following compounds of formula IIIa can be prepared.

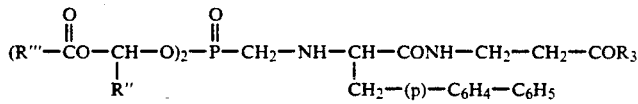

(IIIa)

(a) Ethyl N-{2-[di-(αpropionyloxyisobutyl)-phosphonomethylamino]-3-(4-biphenylyl)-propionyl}-3-aminopropionate, as an oil; being the compound of formula IIIa wherein R″=isopropyl, R‴=ethyl, and $R_3$=ethoxy.

(b) N-{2-[di-(α-propionyloxyisobutyl)-phosphonomethylamino]-3-(4-biphenylyl)-propionyl}-3-aminopropionic acid, as an oil; being the compound of formula IIIa wherein R″=isopropyl, R‴=ethyl and $R_3$=hydroxy.

(c) Ethyl N-{2-[di-(α-propionyloxycyclohexylmethyl)-phosphonomethylamino]-3-(4-biphenylyl)-propionyl}-3-aminopropionate as an oil; being the compound of formula IIIa wherein R″=cyclohexyl, R‴=ethyl and $R_3$=ethoxy.

(d) Ethyl N-{2-[di-(isobutyryloxymethyl)-phosphonomethylamino]-3-(4-biphenylyl)-propionyl}-3-aminopropionate as an oil; being the compound of formula IIIa wherein R″=hydrogen, R‴=isopropyl, and $R_3$=ethoxy.

(e) Ethyl N-{2-[di-(α-isobutyryloxyisobutyl)-phosphonomethylamino]-3-(4-biphenylyl)-propionyl}-3-aminopropionate as an oil, being the compound of formula IIIa wherein R″=isopropyl, R‴=isopropyl, $R_3$=ethoxy.

(f) N-{2-[di-(pivaloyloxymethyl)-phosphonomethylamino]-3-(4-biphenylyl)-propionyl}-3-aminopropionic acid as an oil, being the compound of formula IIIa wherein R″=hydrogen, R‴=t-butyl and $R_3$=hydroxy.

(g) Benzyl N-{2-[di-(α-pivaloyloxyethyl)-phosphonomethylamino]-3-(4-biphenylyl)-propionyl}-3-aminopropionate, as an oil, being the compound of formula IIIa wherein R″=methyl, R‴=t-butyl and $R_3$=benzyloxy.

(h) N-[2-[di-(α-pivaloyloxyethyl)-phosphonomethylamino]-3-(4-biphenylyl)-propionyl}-3-aminopropionic acid, m.p. 45°-55°, being the compound of formula IIIa wherein R″=methyl, R‴=t-butyl and $R_3$=hydroxy.

(i) Ethyl N-{2-[di-(α-benzoyloxycyclohexylmethyl)-phosphonomethylamino]-3-(4-biphenylyl)-propionyl}-3-aminopropionate, m.p. 45°, the compound of formula IIIa wherein R″=cyclohexyl, R‴=phenyl and $R_3$=ethoxy.

(j) 5-Aminopentyl N-{2-[di-(α-propionyloxyisobutyl)-phosphonomethylamino]-3-(4-biphenylyl)-propionyl}-3-aminopropionate, the compound of formula IIIa wherein R″=isopropyl, R‴=ethyl and $R_3$=5-aminopentyloxy.

(k) Decyl N-{2-[di-(α-propionyloxyisobutyl)-phosphonomethylamino]-3-(4-biphenylyl)-propionyl}-3-aminopropionate, the compound of formula IIIa wherein R″=isopropyl, R‴=ethyl and $R_3$=decyloxy;

(l) Ethyl N-{2-[di-(α-pentanoyloxyisobutyl)-phosphonomethylamino]-3-(4-biphenylyl)-propionyl}-3-aminopropionate, the compound of formula IIIa wherein R″=isopropyl, R‴=butyl and $R_3$=ethoxy;

(m) Ethyl N-{2-[di-(α-octanoyloxyisobutyl)-phosphonomethylamino]-3-(4-biphenylyl)-propionyl}-3-aminopropionate, the compound of formula IIIa wherein R″=isopropyl, R‴=heptyl and $R_3$=ethoxy.

(n) Decyl N-{2-[di-(α-octanoyloxyisobutyl)-phosphonomethylamino]-3-(4-biphenylyl)-propionyl}-3-aminopropionate, the compound of formula IIIa wherein R''=isopropyl, R'''=heptyl and R₃=decyloxy.

EXAMPLE 10

A solution of S-(+)-N-{2-[di-(α-propionyloxyisobutyl)-phosphonomethylamino]-3-(4-biphenylyl)-propionyl}-3-aminopropionic acid (0.118 g, 0.18 mmol) in THF (4 mL) is cooled to 0° and treated with sodium trimethylsilanoate (0.178 mL, 0.178 mmol, 1N in THF). The solution is stirred for 30 minutes at 0°, then concentrated under reduced pressure to give sodium S-(+)-N-{2-[di-(α-propionyloxyisobutyl)-phosphonomethylamino]-3-(4-biphenylyl)-propionyl}-3-aminopropionate as a foamy solid; m.p. 54°-60°.

EXAMPLE 11

Ethyl N-{2-[di-(α-propionyloxyisobutyl)-phosphonomethylamino]-3-(4-biphenylyl)-propionyl}-3-aminopropionate (0.44 g; 0.64 mmol) is dissolved in ethanol (10 ml) and the solution is cooled to 0°. 1N Sodium hydroxide (0.60 mmol) is added dropwise over 15 minutes and stirring is continued for 15 minutes. 1N Hydrochloric acid (0.61 ml; 0.61 mmol) is added and the mixture is concentrated under reduced pressure. The gummy solid residue is partitioned between methylene chloride and cold water. The organic layer is separated, dried over sodium sulfate, filtered and concentrated under vacuum. The desired phosphonic acid monoester is purified by flash-chromatography on silica gel eluting with methylene chloride/ethylacetate (3/2), then with methylene chloride/methanol (85/15) to yield ethyl N-{2-[mono-(α-propionyloxyisobutyl)-phosphonomethylamino]-3-(4-biphenylyl)-propionyl}-3-aminopropionate, the compound of formula IIIb

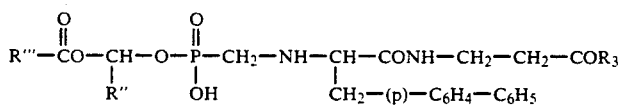 (IIIb)

in which R''=isopropyl, R'''=ethyl and R₃=ethyl, as a diastereoisomeric mixture, m.p. 154°-158°, IR(KBr; cm⁻¹): 3414, 1735, 1684, 1189, 1237, 1092, 1051.

EXAMPLE 12

Similarly to procedure described in example 11, the following compounds can be prepared.
(a) Decyl N-{2-[mono-(α-propionyloxyisobutyl)-phosphonomethylamino}-3-(4-biphenylyl)-propionyl}-3-aminopropionate, m.p. 159°-163°, the compound of formula IIIb wherein R''=isopropyl, R'''=ethyl and R₃=decyloxy;
(b) Ethyl N-{2-[mono(α-pentanoyloxyisobutyl)-phosphonomethylamino}-3-(4-biphenylyl)-propionyl}-3-aminopropionate, m.p. 168°-171°, the compound of formula IIIb wherein R''=isopropyl, R'''=butyl and R₃=ethoxy;
(c) Ethyl N-{2-[mono-(αoctanoyloxyisobutyl)-phosphonomethylamino]-3-(4-biphenylyl)-propionyl}-3-aminopropionate, m.p. 164°-167°, the compound of formula IIIb wherein R''=isopropyl, R'''=heptyl, and R₃=ethoxy;
(d) Ethyl N-{2-[mono(α-benzoyloxyethyl)-phosphonomethylamino]-3-(4-biphenylyl)-propionyl}-3-aminopropionate, m.p. 124°-130° dec., the compound of formula IIIb wherein R''=methyl, R'''=phenyl, and R₃=ethoxy;
(e) Ethyl N-{2-[mono(α-benzoyloxycyclohexylmethyl)-phosphonomethylamino]-3-(4-biphenylyl)-propionyl}-3-aminopropionate, m.p. 152°, the compound of formula IIIb wherein R''=cyclohexyl, R'''=phenyl and R₃=ethoxy;
(f) Decyl N-{2-[mono-(α-octanoyloxyisobutyl)-phosphonomethylamino]-3-(4-biphenylyl)-propionyl}-3-aminopropionate, the compound of formula IIIb wherein R''=isopropyl, R'''=heptyl, and R₃=decyloxy;
(g) 5-Aminopentyl N-{2-[mono(α-propionyloxyisobutyl)-phosphonomethylamino]-3-(4-biphenylyl)-propionyl}-3-aminopropionate isolated as the hydrochloride salt, m.p. 130°-135°, the compound of formula IIIb wherein R''=isopropyl, R'''=ethyl and R₃=5-aminopentyloxy.

The compound of example 12(g) is prepared as follows: N-[2-(dimethylphosphonomethylamino)-3-(4-biphenylyl)-propionyl]-3-aminopropionic acid (700 mg; 1.61 mmol) in dimethyl formamide (DMF) (10 ml) is treated sequentially with N-benzyloxycarbonyl-5-aminopentanol (400 mg; 1.98 mmol) in DMF (2 ml), 1-hydroxybenzotriazole (HOBT) (265 mg; 1.96 mmol), 4-N,N-dimethylaminopyridine (DMAP) (239 mg; 1.96 mmol) and N-(3-dimethylaminopropyl)-N'-ethylcarbodiimide hydrochloride (EDC) (553 mg; 3.22 mmol). The mixture is stirred for 20 hours, then partitioned between ethyl acetate (50 ml) and 1N HCl(30 ml). The organic layer is washed with a saturated solution of sodium bicarbonate (30 ml), then with brine (30 ml) before being dried over anhydrous sodium sulfate. After concentration under reduced pressure, the oily residue is purified by column chromatography on silica gel, eluting first with ethyl acetate, then with 5% methanol in methylene chloride to yield N-benzyloxycarbonyl-5-aminopentyl N-[2-(dimethylphosphonomethyl amino)-3-(4-biphenylyl)-propionyl]-3-aminopropionate as an oil; Rf(SiO2; MeOH/CH2Cl2):0.4.

Such is converted to the free phosphonic acid, esterified to the di-1-propionyloxyisobutylphosphonate, and selectively hydrolyzed, according to methods described in the previous examples, to obtain the corresponding N-benzyloxycarbonyl-5-aminopentyl N-{2-[mono-(α-propionyloxyisobutyl)-phosphonomethylamino]-3-(4-biphenylyl)-propionyl}-3-aminopropionate, the compound of. formula IIIb wherein R''=isopropyl, R'''=ethyl and R₃=N-benzyloxycarbonyl-5-aminopentyloxy.

The above product (150 mg; 0.203 mmol) in methanol (3 ml) is hydrogenated on 10% Pd on carbon (75 mg) during 4 hours in a Parr shaker (3 atmospheres pressure). The catalyst is filtered off and the filtrate is concentrated in vacuo to give the compound of example 12(g).

EXAMPLE 13

Similarly to procedures described in the previous examples, the following compounds can be prepared:

(a) N-{2-[di-(α-propionyloxyisobutyl)-phosphonomethylamino]-3-(4-biphenylyl)-propionyl}-glycine ethyl ester;

(b) Ethyl N-{2-[di-(α-propionyloxyisobutyl)-phosphonomethylamino]-3-(4-biphenylyl)-propionyl}-4-aminobutyrate.

(c) N-{2-[mono-(α-propionyloxyisobutyl)-phosphonomethylamino]-3-(4-biphenylyl)-propionyl}-glycine ethyl ester;

(d) Ethyl N-{2-[mono-(α-propionyloxyisobutyl)-phosphonomethylamino]-3-(4-biphenylyl)-propionyl}-4-aminobutyrate;

(e) N-{2-[di-(α-propionyloxyisobutyl)-phosphonomethylamino]-3-(4-biphenylyl)-propionyl}-glycine.

(f) Benzyl N-{2-[mono-(α-propionyloxyisobutyl)-phosphonomethylamino]-3-(4-biphenylyl)-propionyl}-3-aminopropionate;

(g) N-{2-[mono-(α-propionyloxyisobutyl)-phosphonomethylamino]-3-(4-biphenylyl)-propionyl}-3-aminopropionic acid.

EXAMPLE 14

1,3,4-Tri[(S)-(4-biphenyl)alanyl-β-alanine benzyl ester]-hexahydro-1,3,5-triazine (1 g, 0.8 mmol) is dissolved in toluene (25 mL) and treated with diphenyl phosphite

0.51 ml, 2.66 mmol) under nitrogen atmosphere. The solution is heated at 80° for 2 hours, then stirred at room temperature for 18 hours. The solvent is removed under reduced pressure and the residue is purified by flash-chromatography eluting with hexane/ethyl acetate (55:45). Evaporation of the pure fractions gives a colorless oil that crystallizes by trituration with ether and hexanes to yield benzyl (S)-N-[2-(diphenylphosphonomethylamino)-3-(4-biphenylyl)-propionyl]-3-aminopropionate, m.p. 83°–84°; $[\alpha]_D = -45.93$ (c=1.05, $CH_2Cl_2$), having the formula

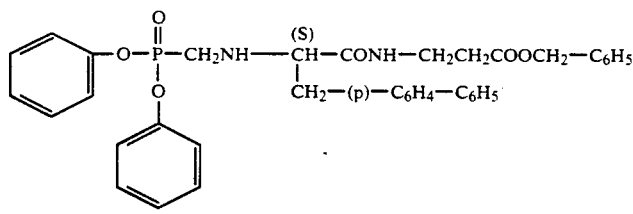

The starting material is prepared as follows:

N-t-butoxycarbonyl-(S)-4-biphenylalanine methyl ester (4.1 g, 11.5 mmol) is dissolved at room temperature in methanolic 1N sodium hydroxide (60 mL). The solution is stirred for 3 hours. Ether (30 mL) and water (30 mL) are added. The aqueous layer is separated and acidified with concentrated HCl, then extracted with ether (2×20 mL) and dried over anhydrous sodium sulfate. Evaporation of the solvent under reduced pressure gives N-t-butoxycarbonyl-(S)-4-biphenylalanine, m.p. 122°–123°.

N-t-butoxycarbonyl-(S)-4-biphenylalanine (10 g, 29 mmol) is dissolved in N,N-dimethylformamide (200 mL) and treated sequentially with hydroxybenzotriazole (4.7 g, 30.4 mmol), triethylamine (5.3 mL, 37.7 mmol), β-alanine benzyl ester p-toluenesulfonate (11.6 g, 34.8 mmol), triethylamine (5.3 mL, 37.7 mmol) and N-dimethylaminopropyl-N'-ethylcarbodiimide hydrochloride (7.2 g, 37.7 mmol). The solution is stirred for 2 hours at room temperature, then poured into ice/water (400 mL) and extracted with ether (2×300 mL). The combined organic layers are washed successively with water (2×150 mL), 1N HCl(100 mL), water (100 mL), sodium bicarbonate (sat., 100 mL). The organic layer is dried over anhydrous sodium sulfate and decolorized with activated carbon. The pale yellow filtrate is concentrated under reduced pressure to give N-t-butoxycarbonyl-(S)(4-biphenyl)-alanyl-β-alanine benzyl ester as a gummy solid. A solution thereof (12.5 g, 24.9 mmol) in ether (200 mL) and methylene chloride (50 mL) at 0° is stirred with gaseous HCl for 5 minutes. Stirring is then continued at room temperature and the disappearance of the starting material is monitored by TLC. After about 2 hours the solid is filtered off and washed with ether before being dried in vacuo to give (S)-(4-biphenyl)-alanyl-β-alanine benzyl ester hydrochloride.

A solution of (S)-(4-biphenyl)-alanyl-β-alanine benzyl ester hydrochloride (10.1 g, 23 mmol) in a 1:1 mixture of ethyl acetate and water (400 mL) is cooled to 0°. Aqueous formaldehyde (37%, 1.73 mL, 23 mmol) is added followed by sodium bicarbonate (1.93 g, 23 mmol). The mixture is stirred at 0° for 1 hour, then at room temperature for 18 hours. The aqueous layer is extracted with ethyl acetate (100 mL). The combined organic layers are washed successively with water (50 mL) and brine (50 mL), then dried over anhydrous sodium sulfate and evaporated in vacuo to give a white solid. Trituration with anhydrous ether (150 mL) followed by drying under vacuum at 45° affords 1,3,5-tri-[(S)-(4-biphenyl)-alanyl-β-alanine benzyl ester]-hexahydro-1,3,5-triazine. This material is used as is in the next step. A small fraction is recrystallized from ethyl acetate-hexane, m.p.=118°–119°; $[\alpha]_D = -8.99$ (c=0.95, $CH_3OH$).

EXAMPLE 15

(a) A solution of benzyl (S)-N-[2-(diphenylphosphonomethylamino)-3-(4-biphenylyl)-propionyl]-3-aminopropionate (1.8 g. 2.77 mmol) in ethyl acetate (30 mL) is hydrogenated in a Parr shaker in the presence of palladium on carbon (10%, 800 mg) at 40 psi for 4 hours. The catalyst is filtered off and washed with methanol (30 mL). After concentration of the filtrate in vacuo, the residue is triturated with ether and the resulting crystalline solid dried under reduced pressure to give (S)-N-[2-(diphenylphosphonomethylamino)-3-(4-biphenylyl)propionyl]-3-aminopropionic acid. It is recrystallized to constant melting point from methanol/ether, m.p. 102°; $[\alpha]_D = -8.99$ (c=0.95, $CH_3OH$).

(b) Similarly prepared according to examples 14 and 15(a) is (R)-N-[2-(diphenylphosphonomethylamino)-3-

(4-biphenylyl)-propionyl]-3-aminopropionic acid, $[\alpha]_D = +9.36°$ (c=0.99, CH$_3$OH).

EXAMPLE 16

(a) 5-Indanol (52.9 mg, 0.394 mmol) is added in one portion to a solution of (S)-N-[2-(diphenylphosphonomethylamino)-3-(4-biphenylyl)-propionyl]-3-aminopropionic acid (200 mg, 0.394 mmol) in methylene chloride (25 ml). 4-(N,N-Dimethylamino)pyridine (48.1 mg, 0.394 mmol) is added followed by N-dimethylaminopropyl-N'-ethylcarbodiimide hydrochloride (151 mg, 0.788 mmol). The solution is stirred at room temperature for 3 hours. Ethyl acetate (60 mL) and water (15 mL) are added. The organic layer is subsequently washed with a saturated solution of sodium bicarbonate (2×15 mL), dried over anhydrous sodium sulfate, filtered and concentrated in vacuo. The residue is purified by flash-chromatography on silica gel, eluting with ethyl acetate-hexane (1:1). Evaporation of the pure fraction yields 5-indanyl (S)-N-[2-(diphenylphosphonomethylamino)-3-(4-biphenylyl)-propionyl]-3-aminopropionate, as a thick colorless oil that can be crystallized from ether, m.p. 89°-91°.

(b) To a stirred solution of (S)-N-[2-(diphenylphosphonomethylamino)-3-(4-biphenylyl)-propionyl]-3-aminopropionic acid (0.6 g, 1.07 mmol) in ethyl acetate (9 mL) is added triethylamine (0.19 mL, 1.34 mmol) followed by 2-chloro-N,N-diethylacetamide (0.18 mL, 1.34 mmol) and sodium iodide (20 mg, 0.13 mmol). The solution is heated under nitrogen at 80° for 12 hours. The precipitate is filtered off and the filtrate is treated with water (10 mL) and 2N HCl (0.5 mL). The organic layer is separated, dried over sodium sulfate and filtered. After evaporation of the solvent under reduced pressure, the semi-solid residue is purified by flash chromatography on silica gel, eluting with ethyl acetate. The title compound is finally crystallized from ethyl acetate-hexane to yield N,N-diethylcarbamoylmethyl (S)-N-[2-(diphenylphosphonomethylamino)-3-(4-biphenylyl)-propionyl]-3-aminopropionate, m.p. 68°-74°, $[\alpha]_D = -20.55$ (c=0.84, CHCl$_3$).

EXAMPLE 17

The following compounds are prepared similarly to procedures described in the previous examples.
(a) (S)-N-{2-[di(4-methylphenyl)phosphonomethylamino]-3-(4-biphenylyl)-propionyl}-3-aminopropionic acid, m.p. 147°-149°;
(b) (S)-N-{2-[di(4-isopropylphenyl)phosphonomethylamino]-3-(4-biphenylyl)-propionyl}-3-aminopropionic acid, m.p. 145°-147°;
(c) (S)-N-{2-[di(4-propylphenyl)phosphonomethylamino]-3-(4-biphenylyl)-propionyl}-3-aminopropionic acid, m.p. 139°-140°;
(d) (S)-N-{2-[di(3,4-dimethylphenyl)phosphonomethylamino]-3-(4-biphenylyl)-propionyl}-3-aminopropionic acid, m.p. 106°-107°;
(e) (S)-N-{2-[di(3,5-dimethylphenyl)phosphonomethylamino]-3-(4-biphenylyl)-propionyl}-3-aminopropionic acid, m.p. 56°-58°;
(f) 2,3-Isopropylideneglyceryl (S)-N-[2-(diphenylphosphonomethylamino)-3-(4-biphenylyl)-propionyl]-3-aminopropionate;
(g) Ethyl (S)-N-[2(-diphenylphosphonomethylamino)-3-(4-biphenylyl)-propionyl]-3-aminopropionate, (oil);
(h) (S)-N-{2-[di(4-methoxyphenyl)-phosphonomethylamino]-3-(4-biphenylyl)-propionyl}-3-aminopropionic acid, m.p. 156°-157°;
(i) Benzyl (S)-N-{2-[di(4-methoxyphenyl)phosphonomethylamino]-3-(4-biphenylyl)-propionyl}-3-aminopropionate, m.p. 74°-75°;
(k) (S)-N-{2-[di(5-indanyl)-phosphonomethylamino]-3-(4-biphenylyl)-propionyl}-3-aminopropionic acid, m.p. 126°-128°;
(l) (S)-N-{2-[di(3-methoxyphenyl)-phosphonomethylamino]-3-(4-biphenylyl)-propionyl}-3-aminopropionic acid, m.p. 52°-54°;
(m) (S)-N-[-2-(diphenylphosphonomethylamino)-3-(4'-chloro-4-biphenylyl)-propionyl]-3-aminopropionic acid;
(n) (S)-N-[2-(diphenylphosphonomethylamino)-3-(4'-methyl-4-biphenylyl)-propionyl]-3-aminopropionic acid;
(o) (S)-N-{2-(diphenylphosphonomethylamino)-3-[4-(2-furanyl)-phenyl]-propionyl}-3-aminopropionic acid;
(p) (S)-N-[2-(diphenylphosphonomethylamino)-3-(4-biphenylyl)-propionyl]-glycine;
(q) (S)-N-[2-(diphenylphosphonomethylamino)-3-(4-biphenylyl)-propionyl]-4-aminobutyric acid;
(r) (S)-N-[2-(diphenylphosphonomethylamino)-3-(4-biphenylyl)-propionyl]-4-aminobenzoic acid;
(s) (S)-N-[2-(diphenylphosphonomethylamino)-3-(4-biphenylyl)propionyl]-7-aminoheptanoic acid;
(t) (S)-N-[2-(diphenylphosphonomethylamino)-3-(4-biphenylyl)-propionyl]-4-aminocyclohexanecarboxylic acid;
(u) (S)-N-{2-[di(4-acetamidophenyl)phosphonomethylamino]-3-(4-biphenylyl)-propionyl}-3-aminopropionic acid;

The starting materials for the above compounds are prepared e.g. according to methods described for starting material of example 14.

EXAMPLE 18

(a) α-(Phenylacetyloxy)-isobutyl benzyl phosphite (hydrogenophosphite) (1.0 g, 2.76 mmol) is refluxed in toluene (70 mL) in the presence of tri[(S)-(4-biphenyl)alanyl-β-alanine ethyl ester]-hexahydro-1,3,5-triazine (896 mg, 0.92 mmol) for 2 hours. Concentration in vacuo affords an oily residue. A mixture of diastereomers is obtained after purification by flash chromatography on silica gel, eluting with ethyl acetate in hexane (1:1). This mixture is dissolved in methanol (10 mL) and hydrogenated at 3 atmospheres pressure over 10% Pd/C for 4 hours. After filtration of the catalyst, the residue is purified by flash-chromatography on silica gel eluting first with ethyl acetate and then with 5% to 30% methanol in methylene chloride. Ethyl (S)-N-{2-mono-(α-phenylacetyloxyisobutyl)-phosphonomethylamino]-3-(4-biphenylyl)-propionyl}-3-aminopropionate, is obtained as a pair of diastereomers, m.p. 148°-150°.

The starting material is prepared as follows:
Dibenzyl phosphite (29.4 g, 112 mmol) is dissolved in a mixture of acetonitrile (140 mL) and water (30 mL) and the reaction mixture is treated with 2.8M aqueous tetramethylammonium hydroxide (40 mL, 112 mmol) at room temperature for 24 hours. After being washed with ether (3×20 mL), the aqueous layer is concentrated in vacuo. The residue is dried under high vacuum at 70° for 12 hours to yield tetramethylammonium benzyl phosphite as a semi-solid. The latter compound (2 g, 8 mmol) and α-(phenylacetoxy)isobutyl bromide (prepared from phenylacetyl bromide and isobutyraldehyde according to Helv. Chim. Acta 61, 2047, 1978) (1.26 mL, 8 mmol) are stirred in acetone (15 mL) for 18 hours at room temperature. The precipitate is filtered through Celite. The filtrate is concentrated under reduced pressure and purified by flash-chromatography on silica gel eluting with 37.5% of ethyl acetate in hexane. Evaporation of the pure fractions gives the unsymmetrical (α-phenylacetyloxyisobutyl) benzyl phosphite as a colorless oil.

(b) Similarly prepared is ethyl (S)-N-{2-[mono(α-octanoyloxyisobutyl)-phosphonomethylamino]-3-(4-biphenylyl)-propionyl}-3-aminopropionate, m.p. 164°–167°.

(c) Similarly prepared is ethyl (S)-N-{2-[mono(α-dodecanoyloxyisobutyl)phosphonomethylamino]-3-(4-biphenylyl)-propionyl}-3-aminopropionate, m.p. 169°–170°.

EXAMPLE 19

(S)-N-[2-(Diphenylphosphonomethylamino)-3-(4-biphenylyl)-propionyl]-3-aminopropionic acid (100 mg, 0.18 mmol) is dissolved in acetonitrile (10 mL) containing 5% 1N HCl. The mixture is refluxed for 3 hours. The precipitate is filtered and triturated with aqueous methanol to yield (S)-N-[2-(monophenylphosphonomethylamino)-3-(4-biphenylyl)-propionyl]-3-aminopropionic acid as a monohydrate, m.p. 222°–223°.

EXAMPLE 20

(a) Dibenzyl phosphite (0.319 mL, 1.44 mmol) and 1,3,5-tri[(S)-(4-biphenyl)alanine benzyl ester]-hexahydro-1,3,5 triazine (500 mg, 0.48 mmol) are dissolved in toluene (25 mL) and refluxed for 2 hours. The solution is concentrated under reduced pressure and the residue is purified by flash chromatography eluting with ethyl acetate to give benzyl (S)-N-[2-(dibenzylphosphonomethylamino)-3-(4-biphenylyl)-propionyl]-3-aminopropionate as an oil. This material is dissolved in 30% HBr in acetic acid (3 mL). The solution is stirred at room temperature for 18 hours and poured into a 3:1 mixture of ether and water (25 mL). The white precipitate is collected and dried in vacuo to give (S)-N-[2-(phosphonomethylamino)-3-(4-biphenylyl)-propionyl]-3-aminopropionic acid of example 2.

(b) Similarly prepared is (R)-N-[2-(phosphonomethylamino-3-(4-biphenylylpropionyl]-3-aminopropionic acid, m.p. 250°–251°. $[\alpha]^{25}_D = -24.95$ (c=0.72, 0.05N NaOH).

EXAMPLE 21

To a stirred solution of (S)-N-[2-(diphenylphosphonomethylamino)-3-(4-biphenylyl)-propionyl]-3-aminopropionic acid (10.8 g, 19.3 mmol) in methanol (150 mL) is added potassium fluoride (11.2 g, 193 mmol) followed by 18-crown-6 (100 mg, 0.38 mmol). The solution is refluxed for 7 minutes in a preheated oil bath then stirred at room temperature for 3 hours. The volume is then reduced to 50 mL by evaporation under reduced pressure. The solution is cooled in an ice bath and treated with 2N hydrochloric acid (55 mL) and water (50 mL). The product is extracted with methylene chloride (3×70 mL). The organic layer is washed with brine then dried over sodium sulfate. The solution is filtered and concentrated in vacuo. The residue is crystallized from ether to give (S)-N-[2-(dimethylphosphonomethylamino)-3-(4-biphenylyl)-propionyl]-3-aminopropionic acid m.p. 122°–123°, $[\alpha]_D = -10.56°$ (c=0.86, CH$_3$OH).

This material is converted to (S)-N-[2-(phosphonomethylamino)-3-(4-biphenylyl)-propionyl]-3-aminopropionic acid with 30% HBr in acetic acid according to the previous examples.

EXAMPLE 22

Methyl (S)-N-[2-(dimethylphosphonomethylamino)-3-(4-biphenylyl)propionyl]-4-aminobenzoate (75 mg, 0.15 mmol) is dissolved in 30% HBr in acetic acid (1.5 mL) and heated at 70° for 10 hours then at room temperature for 6 hours. The dark solution is concentrated in vacuo and the residue is dissolved in 1N sodium hydroxide (1 mL). The solution is decolorized with charcoal and the filtrate is concentrated under reduced pressure. The precipitate obtained after treatment with 1N HCl (1 mL) is filtered and oven-dried at 50° to give (S)-N-[2-(phosphonomethylamino)-3-(4-biphenylyl)-propionyl]-4-aminobenzoic acid as a white solid, m.p. 270°–274°.

The starting material is prepared as follows:

N-t-butoxycarbonyl-(S)-4-biphenylalanine (1.6 g, 4.65 mmol) is dissolved in dry N,N-dimethylformamide (30 mL) and treated successively with methyl 4-aminobenzoate (0.74 g, 4.9 mmol), hydroxybenzotriazole (0.72 g, 4.7 mmol), triethylamine (0.84 mL, 6 mmol) and N-dimethylaminopropyl-N'-ethylcarbodiimide hydrochloride (1.2 g, 6 mmol). The heterogeneous mixture is stirred at room temperature for 18 hours then treated with ice-water (50 mL) and ether (100 mL). The organic layer is decanted, washed with water and sodium bicarbonate and dried over anhydrous sodium sulfate. The filtrate is concentrated under reduced pressure and the residue is purified by chromatography on silica gel, eluting with 5% of methanol in methylene chloride to give N-t-butoxycarbonyl-(S)-(4-biphenyl)-alanyl-4-aminobenzoate methyl ester. The deprotection of the nitrogen with gaseous HCl as described before affords (S)-(4-biphenyl)-alanyl-4-aminobenzoate methyl ester hydrochloride as a white powder. Conversion to the triazine with aqueous formaldehyde, according to the procedure described before, yields 1,3,5-tri-[(S)-(4-biphenyl)-alanyl-4-aminobenzoate methyl ester]-hexahydro-1,3,5-triazine as an amorphous solid.

A solution of the latter compound (0.15 g, 13 mmol) in toluene (5 ml) is heated at 80° in the presence of dimethyl phosphite (0.037 mL, 4.0 mmol) for 2 hours then stirred at room temperature for 18 hours. Concentration under reduced pressure gives a residue that is purified by chromatography on silica gel, eluting with a gradient of ethyl acetate in hexane (50% to 100%). Methyl (S)-N-[2-(dimethylphosphonomethylamino)-3-(4-biphenylyl)-propionyl]-4-aminobenzoate, m.p. 128°–129° is obtained as an amorphous solid.

EXAMPLE 23

(a) Benzyl (S)-N-[2-(diphenylphosphonomethylamino)-3-(4-biphenylyl)propionyl]-3-aminopropionate (720 mg, 1.1 mmol) is dissolved in THF (15 mL) and treated with 2N hydrochloric acid. The solution is stirred at room temperature for 8 hours. The precipitate is filtered. It can be further purified by column chromatography on silica gel, eluting with a mixture of methylene chloride-methanol-acetic acid (95/5/25), to obtain benzyl (S)-N-[2-(monophenylphosphonomethylamino)-3-(4-biphenylyl)-propionyl]-3-aminopropionate m.p. 243°–244°.

Similarly prepared are:

(b) Ethyl (S)-N-[2-(monophenylphosphonomethylamino)-3-(4-biphenyly)propionyl]-3-aminopropionate, m.p. 233°-234°, [α]$_D$=+5.82° (c=1.08, CH$_3$COOH);

(c) Ethyl (S)-N-{2-[mono(4-methylphenyl)phosphonomethylamino]-3-(4-biphenylyl)-propionyl}-3-aminopropionate;

(d) Ethyl (S)-N-{2-[mono(4-isopropylphenyl)phosphonomethylamino]-3-(4-biphenyly)-propionyl}-3-aminopropionate;

(e) Ethyl (S)-N-{2-[mono(4-propylphenyl)phosphonomethylamino]-3-(4-biphenylyl)-propionyl}-3-aminopropionate;

(f) Ethyl (S)-N-{2-[mono(3,4-dimethylphenyl)phosphonomethylamino]-3-(4-biphenylyl)-propionyl}-3-aminopropionate;

(g) Ethyl (S)-N-{2-[mono(3,5-dimethylphenyl)phosphonomethylamino-3-(4-biphenylyl)-propionyl}-3-aminopropionate;

(h) Benzyl (S)-N-{2-[mono(4-methoxyphenyl)phosphonomethylamino]-3-(4-biphenylyl)-propionyl}-3-aminopropionate;

(i) Ethyl (S)-N-{2-[mono(5-indanyl)-phosphonomethylamino]-3-(4-biphenylyl)-propionyl}-3-aminopropionate;

(j) Ethyl (S)-N-{2-[mono(3-methoxyphenyl)-phosphonomethylamino]-3-(4-biphenylyl)-propionyl}-3-aminopropionate;

(k) Ethyl (S)-N-[2-(monophenylphosphonomethylamino)-3-(4'-chloro-4-biphenylyl)-propionyl]-3-aminopropionate;

(l) Ethyl (S)-N-[2-(monophenylphosphonomethylamino)-3-(4'-methyl-4-biphenylyl)-propionyl]-3-aminopropionate;

(m) Methyl (S)-N-[2-(monophenylphosphonomethylamino)-3-(4-biphenylyl)-propionyl]-3-aminopropionate;

(n) (S)-N-[2-(monophenylphosphonomethylamino)-3-(4-biphenylyl)-propionyl]-glycine ethyl ester;

(o) Ethyl (S)-N-[2-(monophenylphosphonomethylamino)-3-(4-biphenylyl)-propionyl]-4-aminobutyrate;

(p) Methyl (S)-N-[2-(monophenylphosphonomethylamino)-3-(4-biphenylyl)-propionyl]-4-aminobenzoate;

(q) Ethyl (S)-N-[2-(monophenylphosphonomethylamino)-3-(4-biphenylyl)-propionyl]-7-aminoheptanoate;

(r) Ethyl (S)-N-[2-(monophenylphosphonomethylamino)-3-(4-biphenylyl)-propionyl]-4-aminocyclohexanecarboxylate;

(s) Ethyl (S)-N-{2-[mono(4-acetamidophenyl)phosphonomethylamino]-3-(4-biphenylyl)-propionyl}-3-aminopropionate;

(t) 5-Indanyl (S)-N-[2-(monophenylphosphonomethylamino)-3-(4-biphenylyl)-propionyl]-3-aminopropionate;

(u) N,N-Diethylcarbamoylmethyl (S)-N-[2-(monophenylphosphonomethylamino)-3-(4-biphenylyl)-propionyl]-3-aminopropionate, m.p. 208°-209°, [α]$_{435}$=−2.60 (c=0.96, DMSO).

EXAMPLE 24

Preparation of 1,000 capsules each containing 50 mg of the active ingredient, as follows:

| | |
|---|---|
| Ethyl N-{2-[mono-(α-octanoyloxyisobutyl)-phosphonomethylamino]-3-(4-biphenylyl)-propionyl}-3-aminopropionate | 50.00 g |
| Lactose | 187.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10-100 mg of the other compounds disclosed and exemplified herein, e.g. the compounds of examples 15(a), 23(b).

What is claimed is:

1. A compound of formula I

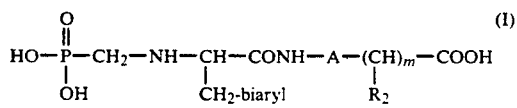

wherein A represents a direct bond, lower alkylene, phenylene or cyclohexylene; m represents 1 or zero, provided that m represents 1 when A is a direct bond; R$_2$ represents hydrogen, hydroxy, lower alkyl, aryl-lower alkyl, C$_5$-C$_7$-cycloalkyl-lower alkyl, amino-lower alkyl, hydroxy-lower alkyl, lower alkylthio-lower alkyl, lower alkoxy-lower alkyl, aryl-lower alkylthio-lower alkyl or aryl-lower alkoxy-lower alkyl; biaryl represents phenyl substituted by carbocyclic or heterocyclic aryl; wherein heterocyclic aryl is selected from the group consisting of thienyl, furanyl, pyridyl, pyrrolyl, and N-(lower alkyl)pyrrolyl or a pharmaceutically acceptable mono-, di- or tri-ester derivative thereof in which one, two or three of the acidic hydroxy groups of the carboxyl and phosphono functional groups are esterified in form of a mono-, di- or tri- pharmaceutically acceptable ester; or a pharmaceutically acceptable amide derivative thereof wherein the carboxyl group is derivatized in form of a pharmaceutically acceptable amide; or a pharmaceutically acceptable salt thereof.

2. A compound of the formula II

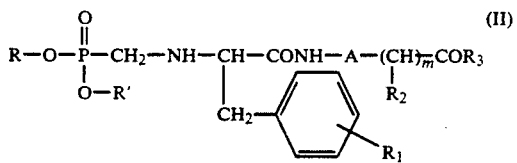

wherein R and R' represent independently hydrogen, carbocyclic aryl, 6-tetrahydronaphthyl, 5-indanyl, acyloxymethyl optionally monosubstituted on methyl carbon by C$_1$-C$_{20}$-alkyl, by C$_5$-C$_7$-cycloalkyl, by aryl or by aryl-lower alkyl; A represents a direct bond, lower alkylene, 1,4-phenylene or 1,4-cyclohexylene; m represents 1 or zero provided that m represents 1 when A is a direct bond; R$_1$ represents phenyl, or phenyl substituted by lower alkyl, lower alkoxy, halogen or trifluoromethyl; or R$_1$ represents thienyl or furanyl optionally substituted by lower alkyl; R$_2$ represents hydrogen, lower alkyl or aryl-lower alkyl; COR$_3$ represents carboxyl or carboxyl derivatized in form of a pharmaceutically acceptable ester or amide; or a pharmaceutically acceptable salt thereof.

3. A compound according to claim 2 wherein $R_1$ is located at the para position.

4. A compound according to claim 3 of formula II wherein R and R' independently represent hydrogen, carbocyclic aryl, (carbocyclic aroyloxy or $C_1$-$C_{20}$-alkanoyloxy)methyl optionally substituted on the methyl carbon by $C_1$-$C_{20}$-alkyl, by $C_5$, $C_6$ or $C_7$-cycloalkyl or by carbocyclic aryl; $R_1$ represents phenyl or phenyl substituted by lower alkyl, lower alkoxy, halogen or trifluoromethyl; A represents linear lower alkylene or a direct bond; m represents 1; $R_2$ represents hydrogen, lower alkyl or aryl-lower alkyl; $COR_3$ represents carboxyl or carboxyl derivatized in form of a pharmaceutically acceptable ester; or a pharmaceutically acceptable salt thereof.

5. A compound according to claim 3 wherein R and R' independently represent hydrogen, $C_1$-$C_{20}$-alkanoyloxymethyl or $C_1$-$C_{20}$-alkanoyloxymethyl substituted on methyl by $C_1$-$C_{20}$-alkyl, by cyclohexyl, by cyclopentyl or by phenyl.

6. A compound according to claim 3 wherein R and R' independently represent hydrogen, 5-indanyl, phenyl, or phenyl substituted by one, two or three substituents selected from lower alkyl, halogen, lower alkoxy, lower alkanoylamino, trifluoromethyl and lower alkoxycarbonyl.

7. A compound according to claim 3 wherein $COR_3$ represents carboxyl, $C_1$-$C_{20}$-alkoxycarbonyl, (carbocyclic or heterocyclic aryl)-lower alkoxycarbonyl, wherein heterocyclic aryl is selected from the group consisting of thienyl, furanyl, pyridyl, pyrrolyl, and N-(lower alkyl)-pyrrolyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl or 1-(lower alkanoyloxy)-lower alkoxycarbonyl.

8. A compound of formula IIa

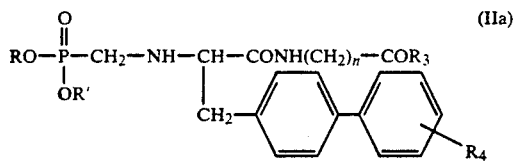

wherein n represents an integer 1 through 6; R and R' independently represent hydrogen, carbocyclic aryl, 5-indanyl or

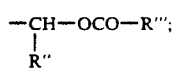

R" represents hydrogen, $C_1$-$C_{20}$-alkyl, $C_5$, $C_6$ or $C_7$-cycloalkyl or carbocyclic aryl; R'" represents $C_1$-$C_{20}$-alkyl, $C_5$, $C_6$ or $C_7$-cycloalkyl, carbocyclic aryl or carbocyclic aryl-lower alkyl; $COR_3$ represents carboxyl, $C_1$-$C_{20}$-alkoxycarbonyl, (carbocyclic or heterocyclic aryl)-lower alkoxycarbonyl, wherein heterocyclic aryl is selected from the group consisting of thienyl, furanyl, pyridyl, pyrrolyl, and N-(lower alkyl)pyrrolyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl; $R_4$ represents hydrogen, lower alkyl, lower alkoxy, halogen or trifluoromethyl; or a pharmaceutically acceptable salt thereof.

9. A compound according to claim 8 wherein n represents the integer 2 or 3.

10. A compound according to claim 9 wherein $COR_3$ represents carboxyl.

11. A compound according to claim 1 of formula III

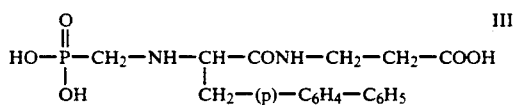

or a pharmaceutically acceptable mono-, di- or tri-ester derivative thereof in which one, two or three of the acidic hydroxy groups of the carboxyl and phosphono functional groups are esterified in form of a mono-, di- or tri-pharmaceutically acceptable ester; or a pharmaceutically acceptable amide derivative thereof wherein the carboxyl group is derivatized in form of a pharmaceutically acceptable amide; or a pharmaceutically acceptable salt thereof; or an optical antipode thereof.

12. A compound according to claim 11 of formula IIIa or IIIb

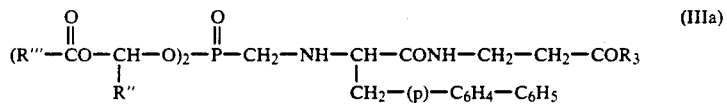

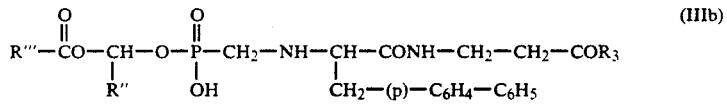

wherein R" and R'" independently represent hydrogen, $C_1$-$C_{20}$-straight chain or branched alkyl, cyclohexyl, cyclopentyl or phenyl; $COR_3$ represents carboxyl; or $COR_3$ represents carboxyl esterified in form of a pharmaceutically acceptable prodrug ester; or a pharmaceutically acceptable salt thereof.

13. A compound according to claim 11 of formula IIIc or IIId

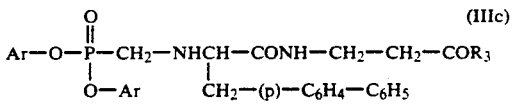

-continued

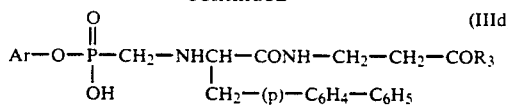

wherein Ar represents phenyl or phenyl substituted by lower alkyl, lower alkoxy, halogen, trifluoromethyl, lower alkanoylamino or lower alkoxycarbonyl; or Ar represents 5-indanyl; $COR_3$ represents carboxyl; or $COR_3$ represents carboxyl esterified in form of a pharmaceutically acceptable prodrug ester; or a pharmaceutically acceptable salt thereof.

14. A compound according to claim 11 having the S-configuration at the asymmetric center in formula III.

15. A compound according to claim 12 wherein $COR_3$ represents carboxyl.

16. A compound according to claim 13 wherein $COR_3$ represents carboxyl.

17. A compound according to claim 11 which is N-[2-(phosphonomethylamino)-3-(4-biphenylyl)-propionyl]-3-aminopropionic acid; the (S)-antipode thereof; or a pharmaceutically acceptable salt of any said compound.

18. A compound according to claim 11 which is N-[2-(diphenylphosphonomethylamino)-3-(4-biphenylyl)-propionyl]-3-aminopropionic acid; the (S)-antipode thereof; or a pharmaceutically acceptable salt of any said compound.

19. A compound according to claim 11 which is N-[2-(monophenylphosphonomethylamino)-3-(4-biphenylyl)-propionyl]-3-aminopropionic acid; the (S)-antipode thereof; or a pharmaceutically acceptable salt of any said compound.

20. A neutral endopeptidase inhibiting pharmaceutical composition comprising an effective neutral endopeptidase inhibiting amount of a compound of claim 1 in combination with one or more pharmaceutically acceptable carriers.

21. A method of treating cardiovascular disorders which comprises administering to a mammal in need of such treatment an effective neutral endopeptidase inhibiting amount of a compound of claim 1 in combination with one or more pharmaceutically acceptable carriers.

* * * * *